US006576232B1

(12) United States Patent
Debinski et al.

(10) Patent No.: US 6,576,232 B1
(45) Date of Patent: Jun. 10, 2003

(54) IL13 MUTANTS

(75) Inventors: Waldemar Debinski, Hershey, PA (US); Jeffrey P. Thompson, Elizabethtown, PA (US)

(73) Assignee: The Penn State Research Foundation

( * ) Notice: Subject to any disclaimer, the term of this patent is extended or adjusted under 35 U.S.C. 154(b) by 0 days.

(21) Appl. No.: 09/679,710

(22) Filed: Oct. 5, 2000

Related U.S. Application Data

(63) Continuation-in-part of application No. 09/054,711, filed on Apr. 3, 1998, now Pat. No. 6,296,843.
(60) Provisional application No. 60/157,934, filed on Oct. 6, 1999.

(51) Int. Cl.[7] ........................ A61K 45/00; A61K 51/00; A61K 39/00; A61K 39/385; C07K 17/00

(52) U.S. Cl. .................. 424/85.2; 424/1.41; 424/185.1; 424/192.1; 424/197.11; 530/351

(58) Field of Search ......................... 530/351; 424/85.2, 424/1.41, 185.1, 192.1, 197.11

(56) References Cited

U.S. PATENT DOCUMENTS

| | | | |
|---|---|---|---|
| 4,671,958 A | | 6/1987 | Rodwell et al. |
| 4,853,332 A | | 8/1989 | Mark et al. |
| 5,458,878 A | | 10/1995 | Pastan et al. |
| 5,614,191 A | | 3/1997 | Puri et al. |
| 5,652,123 A | * | 7/1997 | Caput et al. |
| 5,696,234 A | | 12/1997 | Zurawski et al. |
| 5,919,456 A | * | 7/1999 | Puri et al. |
| 6,296,843 B1 | * | 10/2001 | Debinski |

OTHER PUBLICATIONS

Bramborough et al., "Predictive modelling of the 3–D structure of itnerleukin–13," Prot. Eng., 7:1077–1082 (1994).

Bochner et al., "IL–13 Selectively Induces Vascular Cell Adhesion Molecule–1 Expression in Human Endothelial Cells," J. Immunol., 154:799–803 (1995).

Caput et al., "Clonining and Characterization of a Specific Interleukin (IL)–13 Binding Protein Structurally Related to the IL–5 Receptor α Chain," J. Biol. Chem. 271:16921–16926 (1996).

Chaudhary et al., "Pseudomonas exotoxin contains a specific sequence at the carboxyl terminus that is required for cytotoxicity," Proc. Natl. Acad. Sci., 87:308–312 (1990).

Chaudhary et al., "A Proper Amino Terminus of Diphtheria Toxin is Important for Cytotoxicity," Bioch. Biophys. Res. Comm., 180:545–551 (1991).

Chaudhary et al., "Mutagenesis of Pseudomonas Exotoxin in Indentification of Sequences Responsible for the Animal Toxicity," J. Biol. Chem., 265:16306–16310 (1995).

Debinski et al., "Substitution of Foreign Protein Sequences into a Chimeric Toxin Composed of Transforming Growth Factor α and Pseudomonas Exotoxin," Mol. Cell. Biol., 11:1751–1753 (1991).

Debinski et al., "Monoclonal Antibody C242–Pseudomonas Exotoxin A," J. Clin. Invest., 90:405–411 (1992).

Debinski et al., "A Wide Range of Human Cancers Express Interleukin 4 (IL4) Receptors that can be Targeted with Chimeric Toxin Composed Of IL4 and Pseudomonas Exotoxin," J. Biol. Chem., 268:14065–14070 (1993).

Debinski et al., "Interleukin–4 Receptors Expressed on Tumor Cells May Serve as a Target for Anticancer Therapy Using Chimeric Pseudomonas Exotoxin," Int. J. Cancer 58:744–748 (1994).

Debinski et al., "Recombinant F(ab') C242–Pseudomonas Exotoxin, but not the Whole Antibody–based Immunotoxin, Causes Regression of a Human Colorectal Tumor Xenograft," Clin. Cancer Res., 1:1015–1022 (1994).

Debinski et al., "Human Glioma Cells Overexpress Receptors for Interleukin 13 and are Extremely Sensitive to a Novel Chimeric Protein Composed of Interleukin 13 and Pseudomonas Exotoxin," Clin. Cancer Res., 1:1253–1258 (1995).

Debinski, et al., "A Novel Chimeric Protein Composed of Interleukin 13 and Pseudomonas Exotoxin is Highly Cytotoxic to Human Carcinoma Cells Expressing Receptors for Interleukin 13 and Interleukin 14," J. Biol. Chem., 270:16775–16780 (1995).

Debinski et al., "Receptor for Interleukin (IL) 13 does not Interact with IL4 but Receptor for IL4 Interacts with IL13 on Human Glioma Cells," J. Biol. Chem. 271:22428–22433(1996).

Debinski et al., Novel anti–brain tumor cytotoxins specific for cancer cells, Nature Biotechnology, 16:449–453 (1998).

Heimbrook, et al., "Transforming growth factor α–Pseudomonas exotoxin fusion protein prolongs survival of nude mice bearing tumor xenografts," Proc. Natl. Acad. Sci, 87:4697–4701 (1990).

Hilton et al., "Cloning and characterization of a binding subunit of the interleukin 13 receptor that is also a component of the interleukin 4 receptor," Proc. Natl. Acad. Sci, 93:497–501 (1996).

Husain et al., "Receptor for Interleukin 13 on AIDS–associated Kaposi's Sarcoma Cells Serves as a New Target for a Potent Pseudomonas Exotoxin–based Chimeric Toxin Protein," Clin. Cancer Res., 3:151–156 (1997).

(List continued on next page.)

*Primary Examiner*—Yvonne Eyler
*Assistant Examiner*—Janet L. Andres
(74) *Attorney, Agent, or Firm*—Akerman Senterfitt; Stanley A. Kim

(57) ABSTRACT

This invention provides mutant human interleukin 13 molecules showing varying specificity for the restricted (IL4 independent) IL13 receptor. The mutant hIL13 molecules include those made by substituting the amino acid residues that occur in the alpha-helix regions of native hIL13 with various other amino acid residues. Some of the mutants retain the ability to bind and cause signaling through IL13 receptors, while other mutants do not.

24 Claims, 10 Drawing Sheets

OTHER PUBLICATIONS

Idzerda, et al., "Human Interleukin 4 Receptor Confers Biological Responsiveness and Defines a Novel Receptor Superfamily," J. Exp. Med. 171:861–873 (1990).

Kreitman et al., "Purification and characterization of IL6–PE4E, a recombinant fusion of interleukin 6 with Pseudomonas exotoxin," Bioconjug. Chem., 4:581–585 (1993) [Abstract].

Kruse et al., "Two distinct functional sites of human interleukin 4 are identified by variants impaired in either receptor binding or receptor activation," EMBO J., 12:5121–5129 (1993).

Laske et al., "Tumor regression with regional distribution of the targeted toxin TF–CRM107 in patients with malignant brain tumors," Nature Medicine, 3:1362–1368 (1997).

McKenzie et al., "Interleukin 13, a T–cell–derived cytokine that regulates human monocyte and B–cell function," Proc. Natl. Acad. Sci 90:3735–3739 (1987).

Miloux et al., "Cloning of the human IL–13R$\alpha$1 chain and reconstitution with the IL–4R 60 of a functional IL–4/IL–13 receptor complex," FEBS Letts., 401:163–166 (1997).

Minty et al., "Interleukin–13 is a new human lymphokine regulating inflammatory and immune responses," Nature, 362:248 (1993).

Murata et al., "Structure of IL–13 Receptor: Analysis of Subunit Composition in Cancer and Immune Cells," Biochem. Biophys. Res. Comm., 238:92–94 (1997).

Obiri, et al., "Receptor for Interleukin 13", J. Biol. Chem. 270:8797–8804 (1995).

Pastan, et al., "Recombinant Toxins as Novel Therapeutic Agents," Annu. Rev. Biochem., 61:331–354 (1992).

Phillips et al., "Transforming Growth Factor–$\alpha$—Pseudomonas Exotoxin Fusion Protein )TGF–$\alpha$–PE38) Treatment of Subcutaneous and Intracranial Human Glioma and Medulloblastoma Xenografts in Athymic Mice," Cancer Res., 54:1008–1015 (1994).

Russell et al., "Interleukin–2 Receptor $\gamma$ Chain: A Functional Component of the Interleukin–4 Receptor," Science, 262:1880–1883 (1993).

Schnyder et al., "Interleukin–4 (IL–4) and IL–13 Bind to a Shared Heterodimeric Complex on Endothelial Cells Mediating Vascular Cell Adhesion Molecule–1 Induction in the Absence of the Common $\gamma$ Chain," Blood, 87:4286–4295 (1996).

Seetharam et al., "Increased Cytotoxic Activity of Pseudomonas Exotoxin and Two Chimeric Toxins Ending in KDEL," J. Biol. Chem. 266:17376–17381 (1991).

Siegall et al., "Functional Analysis of Domains II, Ib, and III of Pseudomonas Exotoxin," J. Biol.Chem., 264:14256–142610 (1989).

Sironi, "Regulation of Endothelial and Mesothelial Cell Function by Interleukin–13: Selective Induction of Vascular Cell Adhesion Molecule–1 and Amplification of Interleukin–6 Production," Blood 84:1913–1921 (1994).

Tony et al., "Design of human interleukin–4 antogonists inhibiting interleukin–4–dependent and interleukin–13–dependent responses in T–cells and B–cells with high efficiency," Eur. J. Biochem, 225:659–665 (1994).

Vita et al., "Characterization and Comparison of the Interleukin 13 Receptor with the Interleukin 4 Receptor on Several Cell Types," J. Biol. Chem, 270:3512–3517 (1995).

Wersäll et al., "Introtumoral infusion of the monoclonal antibody, mAb 425, against the epidermal–growth–factor receptor in patients with advanced malignant glioma," Cancer Immunol. Immunother., 44:157–164 (1997).

Zurawski et al., "The Primary Binding Subunit of the Human Interleukin–4 Receptor is also a Component of the Interleukin–13 Receptor," J. Biol. Chem. 270:13869–13878 (1995).

* cited by examiner

FIG.4A
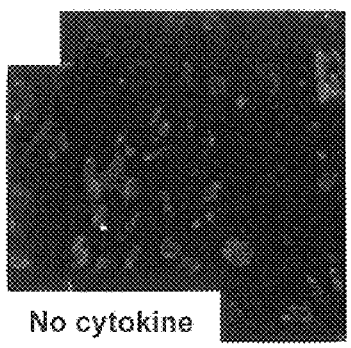
No cytokine
FIG.4B
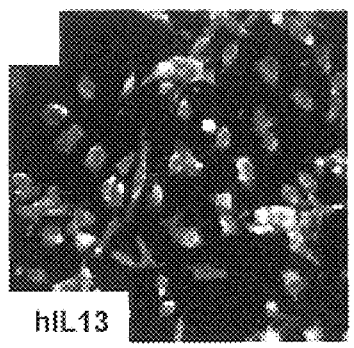
hIL13
FIG.4C
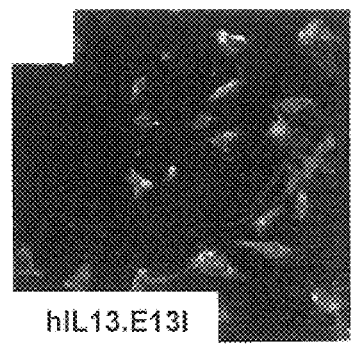
hIL13.E13I
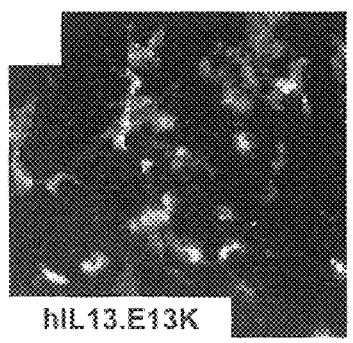
hIL13.E13K
FIG.4D
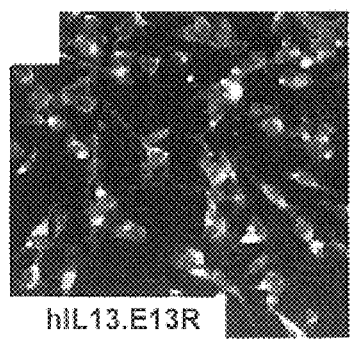
hIL13.E13R
FIG.4E
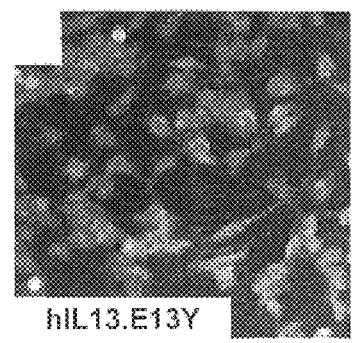
hIL13.E13Y
FIG.4F

SEQUENCE LISTING

<160> NUMBER OF SEQ ID NOS: 23

<210> SEQ ID NO 1
<211> LENGTH: 114
<212> TYPE: PRT
<213> ORGANISM: Homo sapiens

<400> SEQUENCE: 1

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn

<210> SEQ ID NO 2
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Glu to Lys substitution
      at residue 13

<400> SEQUENCE: 2

Ser Pro Gly Pro Val Pro Pro Ser Thr Ala Leu Arg Lys Leu Ile Glu

```
1               5                   10                  15
Glu Leu Val Asn Ile Thr Gln Asn Gln Lys Ala Pro Leu Cys Asn Gly
            20                  25                  30
Ser Met Val Trp Ser Ile Asn Leu Thr Ala Gly Met Tyr Cys Ala Ala
        35                  40                  45
Leu Glu Ser Leu Ile Asn Val Ser Gly Cys Ser Ala Ile Glu Lys Thr
    50                  55                  60
Gln Arg Met Leu Ser Gly Phe Cys Pro His Lys Val Ser Ala Gly Gln
65                  70                  75                  80
Phe Ser Ser Leu His Val Arg Asp Thr Lys Ile Glu Val Ala Gln Phe
                85                  90                  95
Val Lys Asp Leu Leu Leu His Leu Lys Lys Leu Phe Arg Glu Gly Arg
            100                 105                 110
Phe Asn
```

<210> SEQ ID NO 3
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Glu to Ile substitution
      at residue 13

<400> SEQUENCE: 3

```
Ser Pro Gly Pro Val Pro Pro Ser Thr Ala Leu Arg Ile Leu Ile Glu
1               5                   10                  15
Glu Leu Val Asn Ile Thr Gln Asn Gln Lys Ala Pro Leu Cys Asn Gly
            20                  25                  30
Ser Met Val Trp Ser Ile Asn Leu Thr Ala Gly Met Tyr Cys Ala Ala
        35                  40                  45
Leu Glu Ser Leu Ile Asn Val Ser Gly Cys Ser Ala Ile Glu Lys Thr
    50                  55                  60
Gln Arg Met Leu Ser Gly Phe Cys Pro His Lys Val Ser Ala Gly Gln
65                  70                  75                  80
Phe Ser Ser Leu His Val Arg Asp Thr Lys Ile Glu Val Ala Gln Phe
                85                  90                  95
Val Lys Asp Leu Leu Leu His Leu Lys Lys Leu Phe Arg Glu Gly Arg
            100                 105                 110
Phe Asn
```

<210> SEQ ID NO 4
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Glu to Cys substitution
      at residue 13

<400> SEQUENCE: 4

```
Ser Pro Gly Pro Val Pro Pro Ser Thr Ala Leu Arg Cys Leu Ile Glu
1               5                   10                  15
Glu Leu Val Asn Ile Thr Gln Asn Gln Lys Ala Pro Leu Cys Asn Gly
            20                  25                  30
Ser Met Val Trp Ser Ile Asn Leu Thr Ala Gly Met Tyr Cys Ala Ala
        35                  40                  45
Leu Glu Ser Leu Ile Asn Val Ser Gly Cys Ser Ala Ile Glu Lys Thr
```

-continued

```
Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Arg
            100                 105                 110

Phe Asn

<210> SEQ ID NO 5
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Glu to Ser substitution
      at residue 13

<400> SEQUENCE: 5

Ser Pro Gly Pro Val Pro Pro Ser Thr Ala Leu Arg Ser Leu Ile Glu
  1               5                  10                  15

Glu Leu Val Asn Ile Thr Gln Asn Gln Lys Ala Pro Leu Cys Asn Gly
                 20                  25                  30

Ser Met Val Trp Ser Ile Asn Leu Thr Ala Gly Met Tyr Cys Ala Ala
             35                  40                  45

Leu Glu Ser Leu Ile Asn Val Ser Gly Cys Ser Ala Ile Glu Lys Thr
         50                  55                  60

Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Arg
            100                 105                 110

Phe Asn

<210> SEQ ID NO 6
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Glu to Arg substitution
      at residue 13

<400> SEQUENCE: 6

Ser Pro Gly Pro Val Pro Pro Ser Thr Ala Leu Arg Arg Leu Ile Glu
  1               5                  10                  15

Glu Leu Val Asn Ile Thr Gln Asn Gln Lys Ala Pro Leu Cys Asn Gly
                 20                  25                  30

Ser Met Val Trp Ser Ile Asn Leu Thr Ala Gly Met Tyr Cys Ala Ala
             35                  40                  45

Leu Glu Ser Leu Ile Asn Val Ser Gly Cys Ser Ala Ile Glu Lys Thr
         50                  55                  60

Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Arg
```

```
                       100                 105                 110
Phe Asn

<210> SEQ ID NO 7
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Glu to Tyr substitution
      at residue 13

<400> SEQUENCE: 7

Ser Pro Gly Pro Val Pro Pro Ser Thr Ala Leu Arg Tyr Leu Ile Glu
 1               5                  10                  15

Glu Leu Val Asn Ile Thr Gln Asn Gln Lys Ala Pro Leu Cys Asn Gly
             20                  25                  30

Ser Met Val Trp Ser Ile Asn Leu Thr Ala Gly Met Tyr Cys Ala Ala
         35                  40                  45

Leu Glu Ser Leu Ile Asn Val Ser Gly Cys Ser Ala Ile Glu Lys Thr
 50                  55                  60

Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Arg
             100                 105                 110

Phe Asn

<210> SEQ ID NO 8
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Glu to Asp substitution
      at residue 13

<400> SEQUENCE: 8

Ser Pro Gly Pro Val Pro Pro Ser Thr Ala Leu Arg Asp Leu Ile Glu
 1               5                  10                  15

Glu Leu Val Asn Ile Thr Gln Asn Gln Lys Ala Pro Leu Cys Asn Gly
             20                  25                  30

Ser Met Val Trp Ser Ile Asn Leu Thr Ala Gly Met Tyr Cys Ala Ala
         35                  40                  45

Leu Glu Ser Leu Ile Asn Val Ser Gly Cys Ser Ala Ile Glu Lys Thr
 50                  55                  60

Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Arg
             100                 105                 110

Phe Asn

<210> SEQ ID NO 9
<211> LENGTH: 114
<212> TYPE: PRT
<213> ORGANISM: ARTIFICIAL SEQUENCE
```

-continued

```
<220> FEATURE:
<221> NAME/KEY: misc_feature
<223> OTHER INFORMATION: hIL13 mutant having a Glu to Lys substitution
      at residue 16

<400> SEQUENCE: 9

Ser Pro Gly Pro Val Pro Pro Ser Thr Ala Leu Arg Glu Leu Ile Lys
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn

<210> SEQ ID NO 10
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Glu to Lys substitution
      at residue 17

<400> SEQUENCE: 10

Ser Pro Gly Pro Val Pro Pro Ser Thr Ala Leu Arg Glu Leu Ile Glu
1               5                   10                  15

Lys Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn

<210> SEQ ID NO 11
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Arg to Asp substitution
      at residue 66

<400> SEQUENCE: 11

Ser Pro Gly Pro Val Pro Pro Ser Thr Ala Leu Arg Glu Leu Ile Glu
1               5                   10                  15
```

```
Glu Leu Val Asn Ile Thr Gln Asn Gln Lys Ala Pro Leu Cys Asn Gly
             20                  25                  30

Ser Met Val Trp Ser Ile Asn Leu Thr Ala Gly Met Tyr Cys Ala Ala
         35                  40                  45

Leu Glu Ser Leu Ile Asn Val Ser Gly Cys Ser Ala Ile Glu Lys Thr
     50                  55                  60

Gln Asp Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Arg
             100                 105                 110

Phe Asn

<210> SEQ ID NO 12
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Ser to Asp substitution
      at residue 69

<400> SEQUENCE: 12

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
             20                  25                  30

Ser Met Val Trp Ser Ile Asn Leu Thr Ala Gly Met Tyr Cys Ala Ala
         35                  40                  45

Leu Glu Ser Leu Ile Asn Val Ser Gly Cys Ser Ala Ile Glu Lys Thr
     50                  55                  60

Gln Arg Met Leu Asp Gly Phe Cys Pro His Lys Val Ser Ala Gly Gln
65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Arg
             100                 105                 110

Phe Asn

<210> SEQ ID NO 13
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Asp to Lys substitution
      at residue 99

<400> SEQUENCE: 13

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
             20                  25                  30

Ser Met Val Trp Ser Ile Asn Leu Thr Ala Gly Met Tyr Cys Ala Ala
         35                  40                  45

Leu Glu Ser Leu Ile Asn Val Ser Gly Cys Ser Ala Ile Glu Lys Thr
     50                  55                  60
```

```
Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Lys Leu Leu Leu His Leu Lys Lys Leu Phe Arg Glu Gly Arg
            100                 105                 110

Phe Asn

<210> SEQ ID NO 14
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Leu to Ala substitution
      at residue 102

<400> SEQUENCE: 14

Ser Pro Gly Pro Val Pro Pro Ser Thr Ala Leu Arg Glu Leu Ile Glu
 1               5                  10                  15

Glu Leu Val Asn Ile Thr Gln Asn Gln Lys Ala Pro Leu Cys Asn Gly
                 20                  25                  30

Ser Met Val Trp Ser Ile Asn Leu Thr Ala Gly Met Tyr Cys Ala Ala
             35                  40                  45

Leu Glu Ser Leu Ile Asn Val Ser Gly Cys Ser Ala Ile Glu Lys Thr
     50                  55                  60

Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Ala His Leu Lys Lys Leu Phe Arg Glu Gly Arg
            100                 105                 110

Phe Asn

<210> SEQ ID NO 15
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Leu to Ala substitution
      at residue 104

<400> SEQUENCE: 15

Ser Pro Gly Pro Val Pro Pro Ser Thr Ala Leu Arg Glu Leu Ile Glu
 1               5                  10                  15

Glu Leu Val Asn Ile Thr Gln Asn Gln Lys Ala Pro Leu Cys Asn Gly
                 20                  25                  30

Ser Met Val Trp Ser Ile Asn Leu Thr Ala Gly Met Tyr Cys Ala Ala
             35                  40                  45

Leu Glu Ser Leu Ile Asn Val Ser Gly Cys Ser Ala Ile Glu Lys Thr
     50                  55                  60

Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Leu His Ala Lys Lys Leu Phe Arg Glu Gly Arg
            100                 105                 110
```

Phe Asn

<210> SEQ ID NO 16
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Lys to Asp substitution
      at residue 105

<400> SEQUENCE: 16

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Asp Lys Leu Phe Arg Glu Gly Arg
            100                 105                 110

Phe Asn

<210> SEQ ID NO 17
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Lys to Asp substitution
      at residue 106

<400> SEQUENCE: 17

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Asp Leu Phe Arg Glu Gly Arg
            100                 105                 110

Phe Asn

<210> SEQ ID NO 18
<211> LENGTH: 114
<212> TYPE: PRT
<213> ORGANISM: ARTIFICIAL SEQUENCE
<220> FEATURE:

<221> NAME/KEY: misc_feature
<223> OTHER INFORMATION: hIL13 mutant having a Leu to Ala substitution
      at residue 107

<400> SEQUENCE: 18

```
Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Ala Phe Arg Glu Gly Arg
            100                 105                 110

Phe Asn
```

<210> SEQ ID NO 19
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Phe to Tyr substitution
      at residue 108

<400> SEQUENCE: 19

```
Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Tyr Arg Glu Gly Arg
            100                 105                 110

Phe Asn
```

<210> SEQ ID NO 20
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Arg to Asp substitution
      at residue 109

<400> SEQUENCE: 20

```
Ser Pro Gly Pro Val Pro Pro Ser Thr Ala Leu Arg Glu Leu Ile Glu
1               5                   10                  15
```

```
Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Asp Glu Gly Arg
                100                 105                 110

Phe Asn

<210> SEQ ID NO 21
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Arg to Asp substitution
      at residue 112

<400> SEQUENCE: 21

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Asp
                100                 105                 110

Phe Asn

<210> SEQ ID NO 22
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having a Phe to Asp substitution
      at residue 113

<400> SEQUENCE: 22

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60
```

```
Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Arg
             100                 105                 110

Asp Asn

<210> SEQ ID NO 23
<211> LENGTH: 114
<212> TYPE: PRT
<213> ORGANISM: ARTIFICIAL SEQUENCE
<220> FEATURE:
<221> NAME/KEY: misc_feature
<223> OTHER INFORMATION: hIL13 mutant having an Asn to Asp substitution
      at residue 113

<400> SEQUENCE: 23

Ser Pro Gly Pro Val Pro Pro Ser Thr Ala Leu Arg Glu Leu Ile Glu
 1               5                  10                  15

Glu Leu Val Asn Ile Thr Gln Asn Gln Lys Ala Pro Leu Cys Asn Gly
             20                  25                  30

Ser Met Val Trp Ser Ile Asn Leu Thr Ala Gly Met Tyr Cys Ala Ala
             35                  40                  45

Leu Glu Ser Leu Ile Asn Val Ser Gly Cys Ser Ala Ile Glu Lys Thr
         50                  55                  60

Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Arg
             100                 105                 110

Phe Asp
```

IL13 MUTANTS

CROSS-REFERENCE TO RELATED APPLICATIONS

The present application is a continuation-in-part of U.S. patent application Ser. No. 09/054,711, filed on Apr. 3, 1998, which issued as U.S. Pat. No. 6,296,843, and is related to and claims the benefit of U.S. provisional patent application number 60/157,934 filed Oct. 6, 1999.

STATEMENT AS TO RIGHTS TO INVENTIONS MADE UNDER FEDERALLY SPONSORED RESEARCH AND DEVELOPMENT

This invention was made in part with Government support under grant CA741145 awarded by the National Institutes of Health. The Government may have certain rights in the invention.

BACKGROUND OF THE INVENTION

Human interleukin 13 (hIL13) is a 114 amino acid cytokine secreted by activated T cells. Minty et al. (1993) Nature, 362:248–250; and McKenzie et al. (1993) Proc. Natl. Acad. Sci. USA, 90:3735–3739. hIL13 is involved in regulating several different physiological responses. Among these, hIL13 has been shown to downregulate the production of cytokines involved in inflammation. Minty et al., supra; and de Waal Malefyt et al. (1993) J. Immunol., 151:6370–6381. It has also been shown to upregulate expression of major histo-compatibility class II molecules and CD23 on monocytes, and to regulate various aspects of B cell function De Waal Malefyt et al. (1993) Res. Immunol. 144:629–633; McKenzie et al., supra; and de Waal Malefyt et al. (1993) J. Immunol., 151:6370–6381. In addition to regulating cells of the immune system, IL-13 has also been shown to act on other cell types. For example, IL13 has been shown to modulate expression of vascular cell adhesion molecule-1 (VCAM-1) on endothelial cells. Sironi et al. (1994) Blood, 84:1913–1921; Bochner et al. (1995) J. Immunol., 154:799–803; and Schnyder et al. (1996) Blood, 87:4286–4295.

Based on its predicted secondary structure, hIL13 has been added to a growing family of growth hormone-like cytokines that all exhibit bundled alpha-helical core topology. Bamborough et al. (1994) Prot. Engin., 7:1077–1082. Structural analyses indicated that hIL13 is a globular protein comprised mainly of four alpha-helical regions (helices A, B, C, and D) arranged in a "bundled core." Miyajima et al. (1992) Ann. Rev. Immunol., 10, 295–331.

While dissimilar at the primary amino acid level, hIL13 and human interleukin 4 (hIL4) bind and signal through a shared receptor complex. Zurawski et al. (1993) EMBO J., 12:2663–2670; and Tony et al. (1994) Eur. J. Biochem., 225:659–66. This shared receptor is a heterodimer that includes a first subunit of approximately 140 kDa termed p140, and a second subunit of approximately 52 kDa termed α' or IL13Rα1. Idzerda et al. (1990) J. Exp. Med., 173:861–873; Obiri et al. (1995) J. Biol. Chem., 270:8797–8804; Hilton et al. (1996) Proc. Natl. Acad. Sci. USA, 93:497–501; and Miloux et al. (1997) FEBS Letters, 401:163–166. Unlike hIL4, hIL13 does not bind p140 in the absence of α'. Vita et al. (1995) J. Biol. Chem., 270:3512–3517. In addition to the shared receptor, another hIL13 receptor termed the restricted (IL4 independent) receptor exists. In contrast to the shared receptor, the latter receptor binds hIL13 but not hIL4. The restricted receptor is also sometimes called the glioma-associated receptor because it is preferentially expressed at high levels in certain malignant cells, including high grade human gliomas. Debinski et al. (1995) Clin. Cancer Res., 1:1253–1258; and Debinski et al. (1996) J. Biol. Chem., 271, 22428–22433. In addition to being associated with malignancies, hIL13 has also been associated with other pathological conditions. Notably, IL13 has been shown to be involved in pathways that regulate airway inflammation, suggesting that this cytokine might play an important role in asthma and perhaps other allergic pathologies. Webb et al., (2000) J. Immunol.165:108–113; and Djukanovic, R. (2000) Clin. Exp. Allergy 30 Suppl 1:46–50.

SUMMARY OF THE INVENTION

The invention relates to the development and characterization of several mutants of hIL13. Using these mutants, three regions of native hIL13 were identified as being required for signaling through the shared receptor. These regions were localized to alpha-helices A, C and D and were generally separated from the regions involved in binding to the restricted receptor. Glutamic acids at positions 13 and 16 in hIL13 alpha-helix A, arginine and serine at positions 66 and 69 in helix C, and arginine at position 109 in helix D were found to be important in inducing biological signaling because these mutations resulted in the loss and/or gain of functional phenomena.

Mutants within the invention include those having one or more of the native amino acids of hIL13 at positions 13, 16, 17, 66, 69, 99, 102, 104, 105, 106, 107, 108, 109, 112, 113, and 114 replaced with a different amino acid. These mutants are expressed herein as hIL13$X_1$P$X_2$, where P is a number corresponding to the position of the mutated amino acid in hIL13, $X_1$ is the letter abbreviation of the amino acid that was replaced, and $X_2$ is the letter abbreviation of the replacement amino acid. For example, hIL13.E13K represents a mutant form of hIL13 that has the glutamic acid residue that naturally occurs at position 13 in native hIL13 replaced with a lysine residue. Representative mutants within the invention include hIL13.E13K, hIL13.E13I, hIL13.E13C, hIL13.E13S, hIL13.E13R, hIL13.E13Y, hIL13.E13D, hIL13.E16K, hIL13.E17K, hIL13.R66D, hIL13.S69D, hIL13.D99K, hIL13.L102A, hIL13.L104A, hIL13.K105D, hIL13.K106D, hIL13.L107A, hIL13.F108Y, hIL13.R109D, hIL13.R112D, hIL13.F113D, and hIL13.N114D.

Also within the invention are compositions including a mutant hIL13 having an amino acid sequence having at least 90% sequence identity to native hIL13 (SEQ ID NO:1). Such mutants can have a mutation in a domain corresponding to the A, C, or D alpha-helices of native hIL13. Exemplary mutants include those with a polypeptide having an amino acid sequence of one of SEQ ID NOs: 2–23.

Mutants of hIL13 within the invention can be those that specifically bind the shared IL4/IL13 receptor but not the restricted (IL4-independent) receptor; those that specifically bind the restricted (IL4-independent) receptor but not the shared IL4/IL13 receptor; or those that bind both receptors.

Some hIL13 mutants of the invention specifically bind to an hIL13 receptor associated with a cell in a manner that induces a measurable change in the cell's physiology. This change can be of greater or less magnitude than a change in the cell's physiology that would be induced by specifically binding the IL13 receptor with native hIL13.

Compositions within the invention can include both an hIL13 mutant and a pharmaceutically acceptable carrier.

Mutants of hIL13 within the invention can be conjugated to an effector molecule such as a cytotoxin (e.g., Pseudomonas exotoxin, PE38QQR, PE1E, PE4E, Diptheria toxin, ricin, abrin, saporin, and pokeweed viral protein), a detectable label (e.g., radionuclide), an antibody, a liposome, or a lipid.

In another aspect the invention includes a purified nucleic acid encoding a mutant hIL13. Also within the invention is an antibody that specifically binds a mutant hIL13 molecule, but not a native hIL13 molecule. And in another aspect, the invention features a method of delivering a mutant hIL13 to a cell. The method can include the steps of: providing a mutant hIL13 and a cell; and contacting the cell with the mutant hIL13.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994.

As used herein, the phrase "native hIL13" means the mature form of human interleukin 13, the amino acid sequence of which is shown herein as SEQ ID NO:1.

The phrase "hIL13 mutant" or a "mutant hIL13 molecule" means an hIL13 in which one or more of the amino acids differ from the corresponding amino acids in the native hIL13. Thus, for example, where a native hIL13 has a glutamic acid at position 13, a mutant hIL13 can have an amino acid other than glutamic acid at position 13 (e.g., glutamic acid is substituted with lysine). It will appreciated that mutant IL13 molecules of this invention include mutant IL13 molecules of other mammalian species (e.g., rat, murine, porcine, ovine, goats, non-human primates, bovine, canus, and the like) and this invention contemplates the use of mutant IL13 in veterinary as well as human medical conditions.

As used herein, the terms "protein" and "polypeptide" are used synonymously to mean any peptide-linked chain of amino acids, regardless of length or post-translational modification, e.g., glycosylation or phosphorylation. An "purified" polypeptide is one that has been substantially separated or isolated away from other polypeptides in a cell, organism, or mixture in which the polypeptide occurs (e.g., 30, 40, 50, 60, 70, 80, 90, 95, 96, 97, 98, 99, 100% free of contaminants).

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an alanine in each of two polypeptide molecules, then the molecules are identical at that position. For example, if 7 positions in a sequence 10 amino acids in length are identical to the corresponding positions in a second 10 amino acid sequence, then the two sequences have 70% sequence identity. Sequence identity is typically measured using sequence analysis software (e.g., Sequence Analysis Software Package of the Genetics Computer Group, University of Wisconsin Biotechnology Center, 1710 University Avenue, Madison, Wis. 53705).

By the term "antibody" is meant an immunoglobulin as well as any portion or fragment of an immunoglobulin whether made by enzymatic digestion of intact immunoglobulin or by techniques in molecular biology. The term also refers to a mixture containing an immunoglobulin (or portion or fragment thereof) such as an antiserum.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), the specified ligand or antibody binds to its particular "target" (e.g. an IL13 specifically binds to an IL13 receptor) and does not bind in a significant amount to other proteins present in the sample or to other proteins to which the ligand or antibody may come in contact in an organism. Generally, a first molecule that "specifically binds" a second molecule has a binding affinity greater than about $10^5$ (e.g., $10^6$, $10^7$, $10^8$, $10^9$, $10^{10}$, $10^{11}$, and $10^{12}$ or more) moles/liter for that second molecule.

A "mutation" in a polypeptide refers to the substitution of an amino acid at a particular position in a polypeptide with a different amino acid at that position. Thus, for example, the mutation hIL13.E13K indicates that the native amino acid at position 13 in IL13 (glutamic acid, E) is replaced with lysine (K). In some cases, a mutation can be the deletion, addition, or substitution of more than one amino acid in a polypeptide. The mutation does not require an actual removal and substitution of the amino acid(s) in question. The protein can be created de novo with the replacement amino acid in the position(s) of the desired mutation(s) so the net result is equivalent to the replacement of the amino acid in question.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 1 is a photograph of a SDS-PAGE (A) and Western blot (B) analysis of purified hIL13 and various hIL13 mutants. Five hundred nanograms of each purified cytokine was loaded per sample. Proteins were detected using a Coomassie Blue stain, panel A. Separated proteins from a duplicate gel were electroblotted to a PVDF membrane and detected with an anti-hIL13 antibody in a Western blot protocol using an enhanced chemiluminescence detection system, panel B.

FIG. 2 is circular dichroism (CD) spectra obtained from purified hIL13 (A) and various hIL13 mutants (A, B, C). Each protein was diluted in PBS (0.1 mg/ml), thermally equilibrated to 37° C., and its CD spectrum recorded over the wavelength range of 185 nm to 260 nm. The CD spectrum of unfolded hIL13 (panel D) was obtained by diluting the protein in 8 M urea containing 40 mM dithiothreitol prior to analysis. The reported spectra were the average of three consecutive measurements. The mutants in each panel, listed from top to bottom, represent the order of the spectra in each panel, from top to bottom.

Figure 3A:
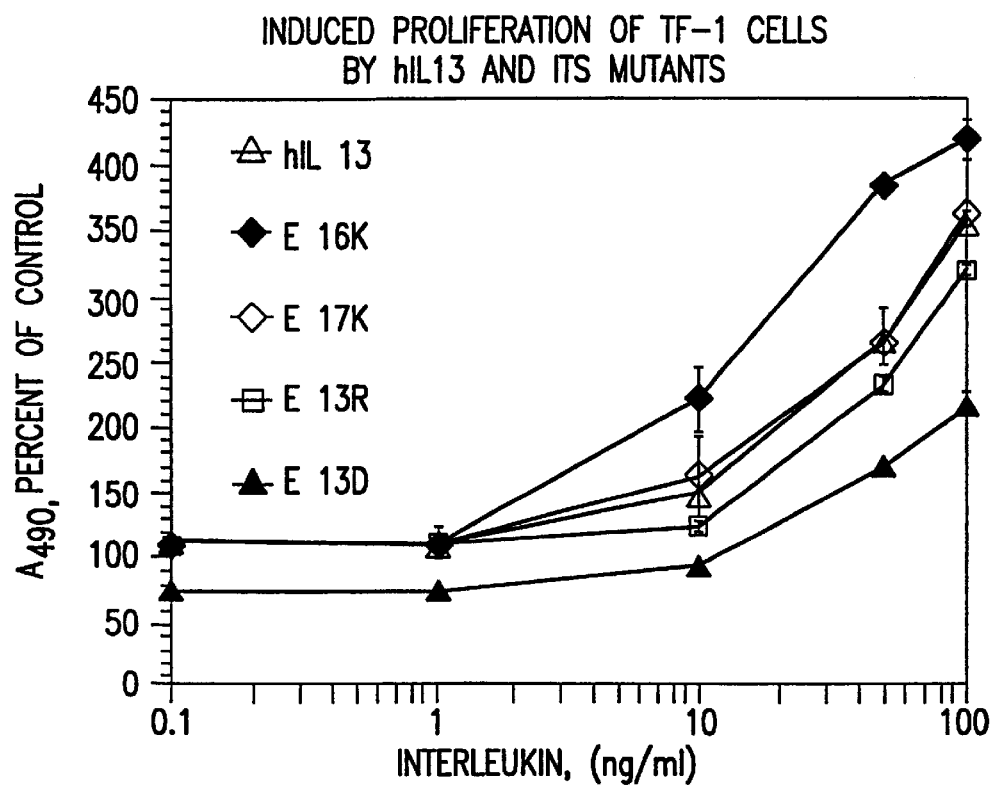
Figure 3B:
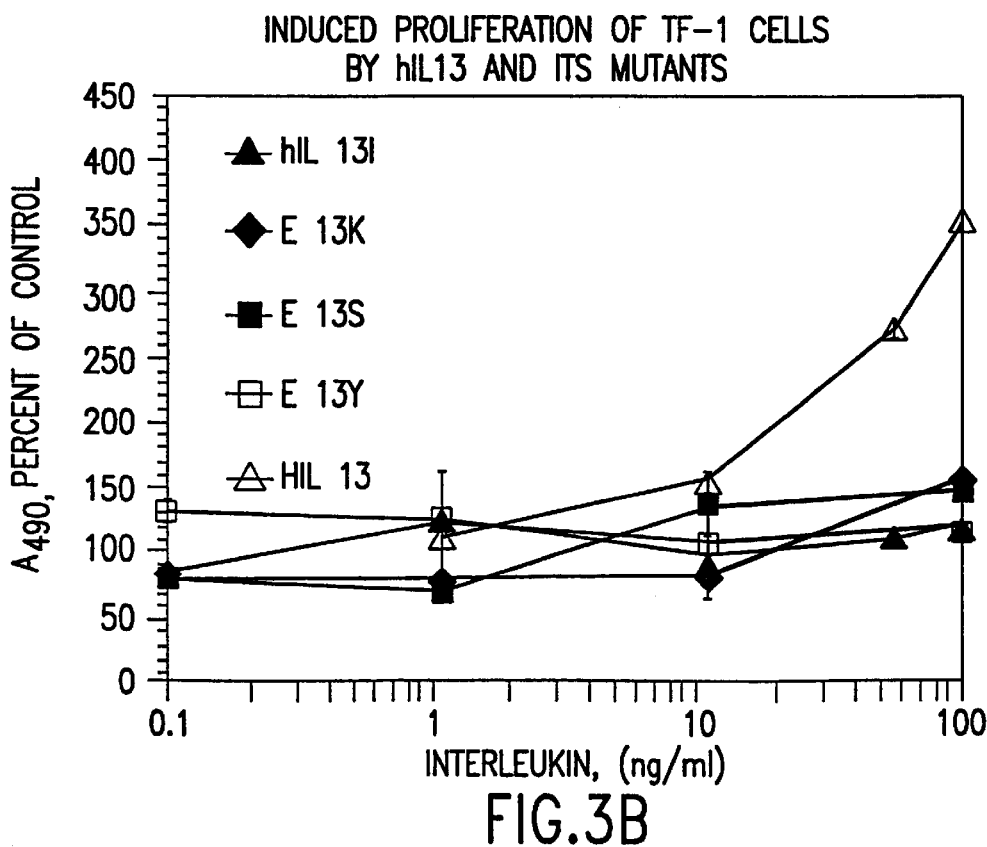
Figure 3C:
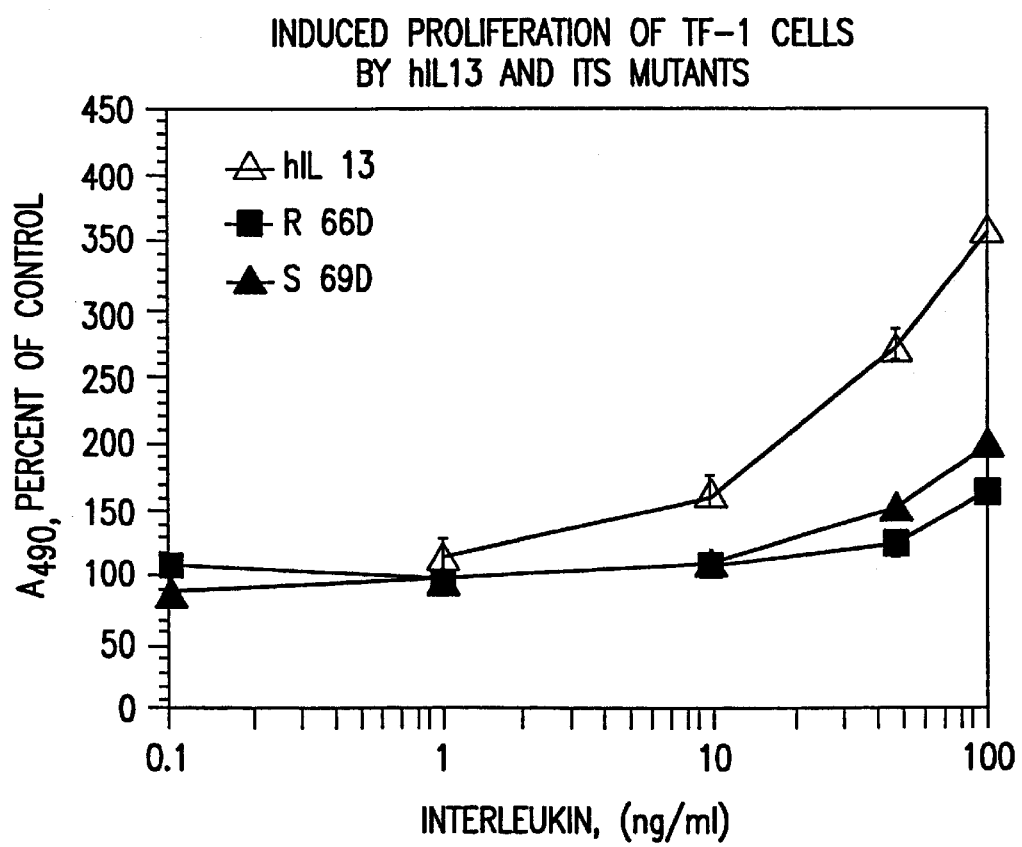

FIG. 3 is graphical representations of data obtained from proliferation assays using TF-1 cells induced with hIL13 and various hIL13 mutants. TF-1 cells were cultured in the presence of increasing concentrations of the indicated protein for 72 h. The amount of TF-1 cell proliferation, compared to control experiments induced with buffer alone, was determined colorimetrically. The reported data is the average of triplicate samples with the error bars representing the standard deviation within a data set. Experiments were repeated several times. Panels represents hIL13 alpha-helix A mutants that increased TF-1 cell proliferation (A), hIL13 alpha-helix A mutants that failed to increase TF-1 cell proliferation (B), and hIL13 alpha-helix C mutants that failed to increase TF-1 cell proliferation (C).

Figures 4G, 4H, 4I, 4J:
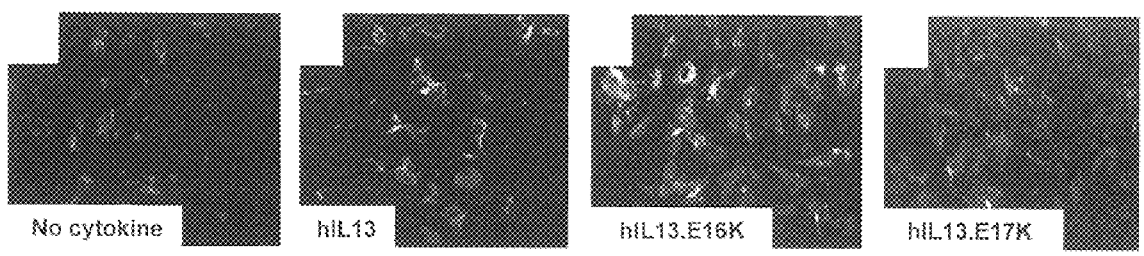
Figure 5A:
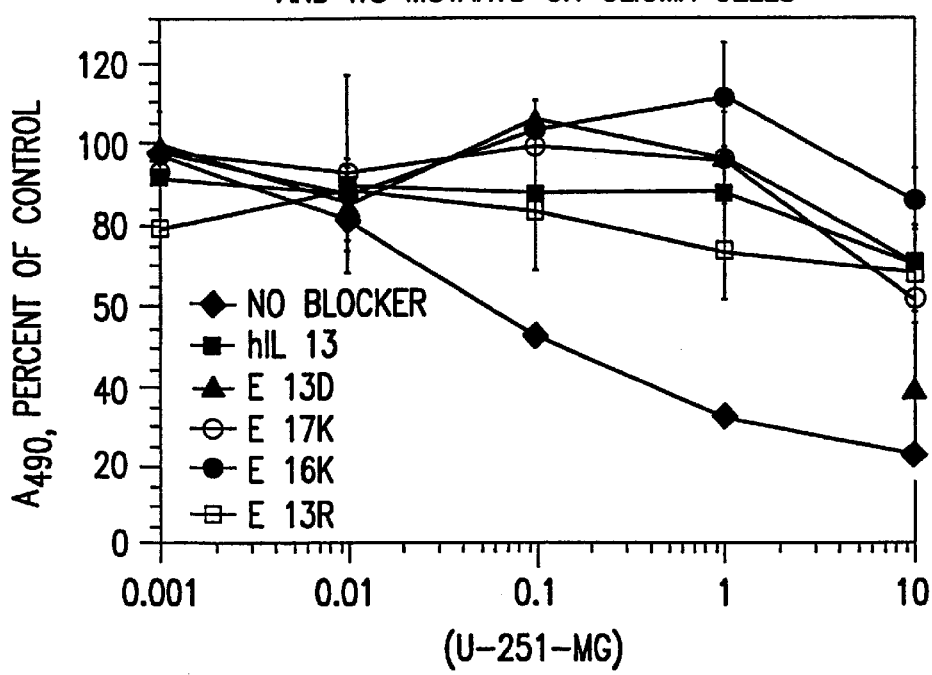
Figure 5B:
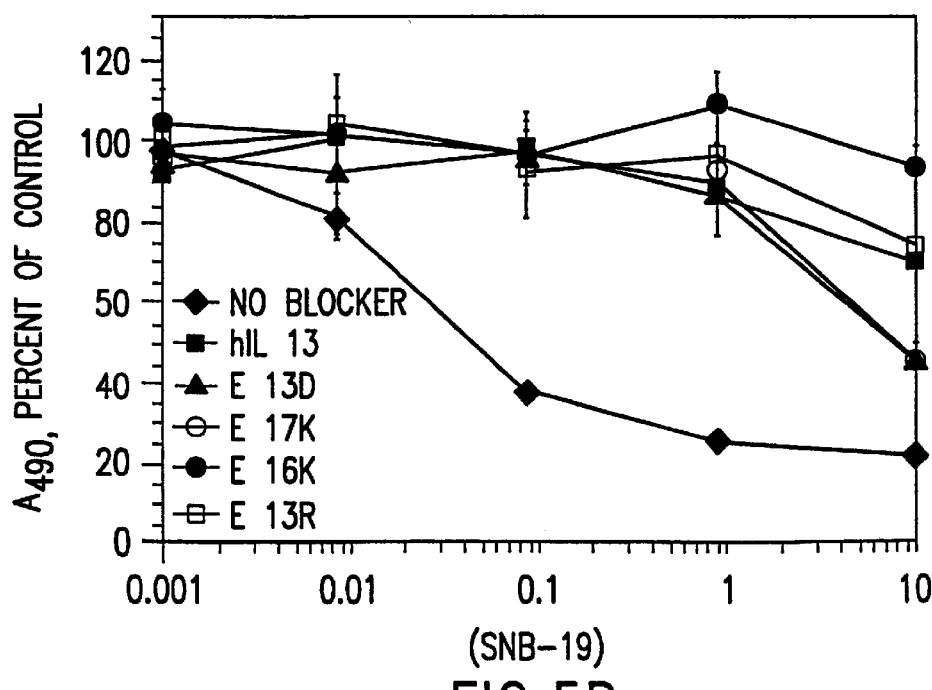
Figure 5C:
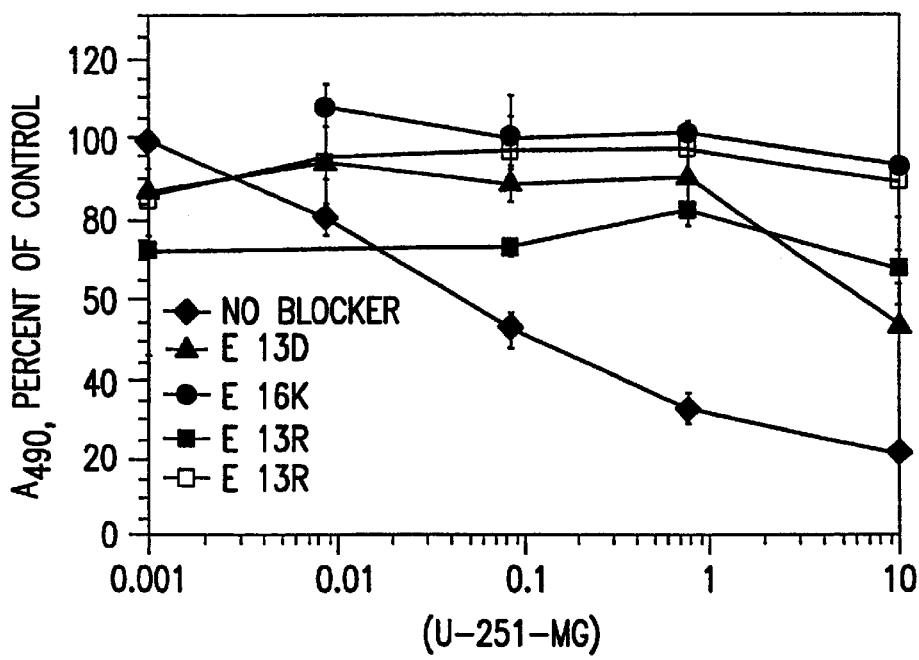
Figure 5D:
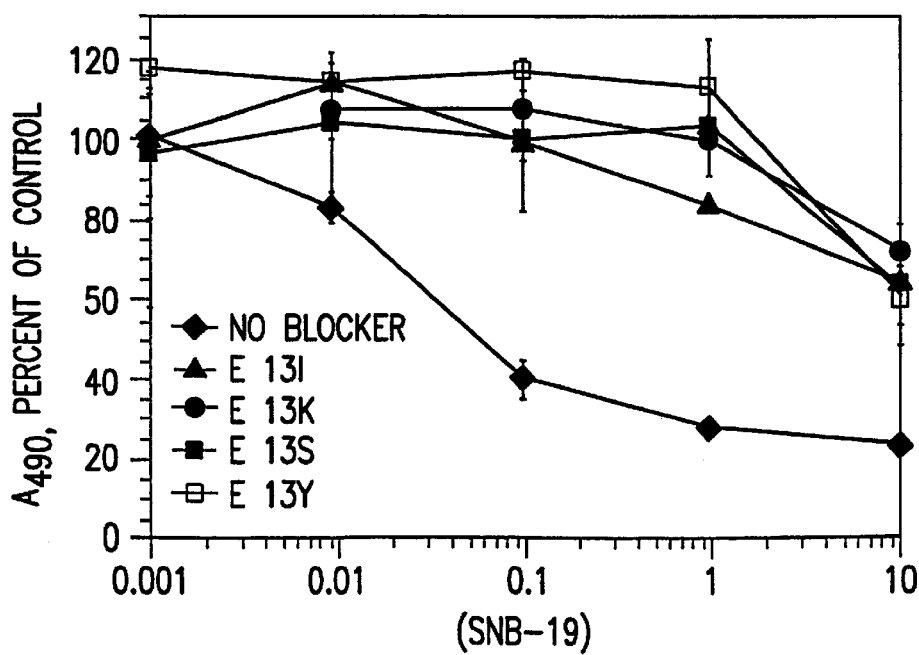
Figure 5E:
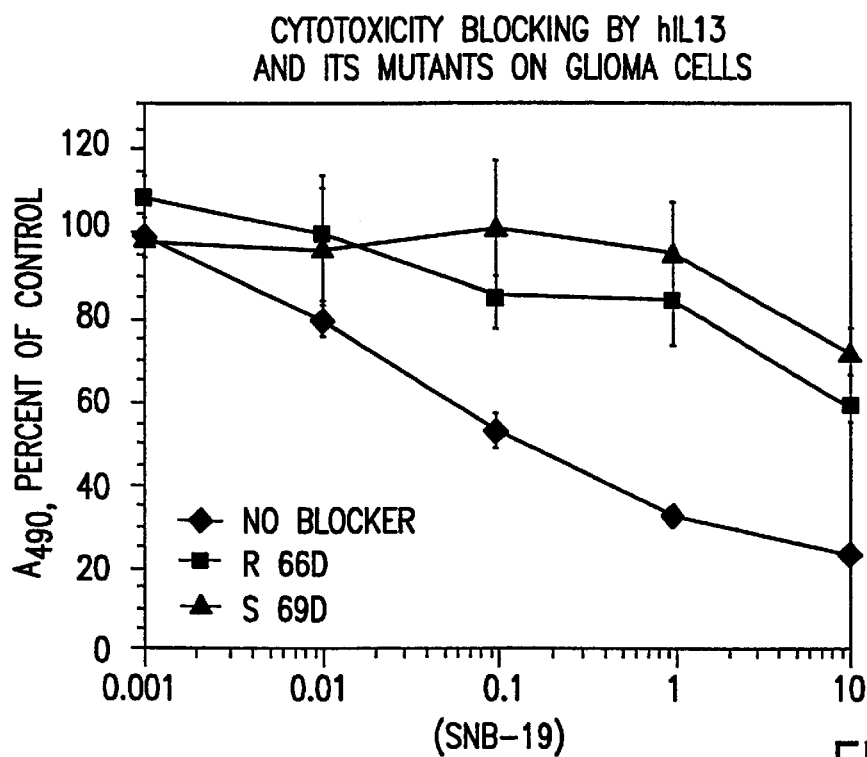
Figure 5F:
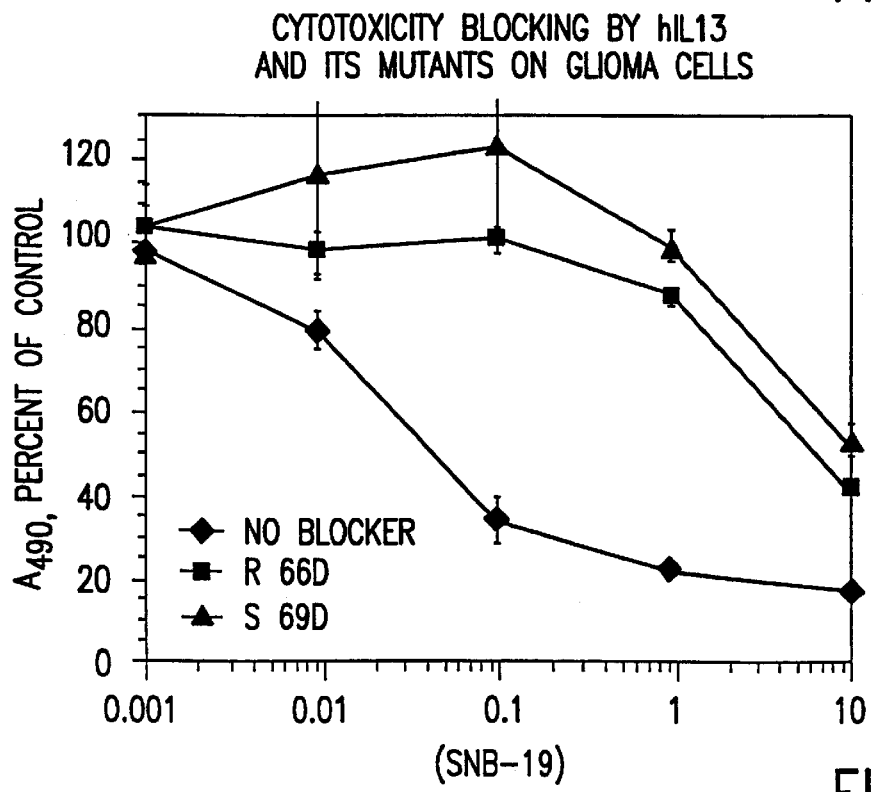

FIG. 4 is a series of photomicrographs of indirect immunofluorescence analyses of HUVEC for VCAM-1 expression induced by hIL13 and various hIL13 mutants. Panels A–F and G–J are from two separate experiments, each with its own set of controls. HUVEC cells were cultured overnight in media containing buffer alone (panels A and G) or 1 mg/ml of either wild-type hIL13 (panels B and H) or various mutants (panels C–F, I and J). Induced expression of the protein was detected through a rhodamine filter using goat anti-VCAM-1 IgG primary antibody and rabbit anti-goat IgG CY3-conjugated secondary antibody. The sensitivity of the imaging camera was set to detect the level of fluorescence in the control field, panels A and G. No further adjustments were made to the sensitivity, allowing for the amount of increased or decreased fluorescence in the experimental fields to be directly related to the amount of interleukin-induced VCAM-1 expression. Photomicrographs are shown at 20X magnification (20X).

FIG. 5 is graphical representations of data obtained from cytotoxicity assays performed to assess the ability of hIL13 and hIL13 mutants to block the killing of U-251MG (panel A) and SNB-19 (panel B) cells by hIL13-PE1E. Cultured cells were incubated with buffer alone, shown in all panels by closed diamonds, or 1 mg/ml of hIL13 or the indicated mutant for 1 hour at 37° C., prior to the addition of increasing concentrations of hIL13-PE1E. The reported data is the average of triplicate samples with the error bars representing the standard deviation within a data set. Experiments were repeated several times.

DETAILED DESCRIPTION

This invention encompasses compositions and methods relating to hIL13 mutants. The below described preferred embodiments illustrate adaptations of these compositions and methods. Nonetheless, from the description of these embodiments, other aspects of the invention can be made and/or practiced based on the description provided below.

BIOLOGICAL METHODS

Methods involving conventional molecular biology techniques are described herein. Such techniques are generally known in the art and are described in detail in methodology treatises such as Molecular Cloning: A Laboratory Manual, 2nd ed., vol. 1–3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. PCR-primer pairs can be derived from known sequences by known techniques such as using computer programs intended for that purpose (e.g., Primer, Version 0.5, ©1991, Whitehead Institute for Biomedical Research, Cambridge, Mass.). The Reverse Transcriptase Polymerase Chain Reaction (RT-PCR) method used to identify and amplify certain polynuleotide sequences within the invention was performed as described in Elek et al., In Vivo, 14:172–182, 2000). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Innunology, ed. Coligan et al., John Wiley & Sons, New York, 1991; and Methods of Immunological Analysis, ed. Masseyeff et al., John Wiley & Sons, New York, 1992.

Mutant hIL13 Molecules

The mutant hIL13 molecules of the invention are based on the amino acid sequence of native hIL13 (SEQ ID NO:1). The hIL13 mutants within the invention differ by one or more amino acids from native hIL13. For example, hIL13 mutants within the invention can have 90% or more (e.g., 91, 92, 93, 94, 95, 96, 97, 98, and 99%) sequence identity with native hIL13. Examples of hIL13 mutants within the invention are those having the amino acid sequences of SEQ ID NOs:2–23. These mutants each have a mutation in a domain corresponding to either the A (residues 9–25 of SEQ ID NO:1), C (residues 59–71 of SEQ ID NO:1), or D (residues 97–113 of SEQ ID NO:1) alpha-helices of native hIL13. Each of these features a substitution of one of the amino acid residues that occurs in native hIL13. Other hIL13 mutants within the invention are those with two or more (e.g., 3, 4, 5, 6, 7, 8, 9,10 or more) such amino acid substitutions, as well as deletion (e.g., truncation) and addition (i.e., those with additional amino acids added to the native hIL13 sequence) mutations.

Mutants of hIL13 can be made in a number of ways by adapting techniques well known in the art. See, e.g., Sambrook et al., supra; and Ausubel et al., supra. For example, starting with the known amino acid sequence of hIL13 (i.e., SEQ ID NO:1), the skilled artisan can chemically synthesize various mutant hIL13 molecules using, e.g, automated commercial polypeptide synthesizers. Techniques for solid phase synthesis of polypeptides are well known. See, e.g., Barany and Merrifield, *Solid-Phase Peptide Synthesis;* pp. 3–284 in The Peptides: *Analysis, Synthesis, Biology. Vol. 2: Special Methods in Peptide Synthesis, Part A.,* Merrifield, et al., *J. Am. Chem. Soc.,* 85: 2149–2156 (1963), and Stewart et al., *Solid Phase Peptide Synthesis,* 2nd ed. Pierce Chem. Co., Rockford, Ill. (1984). Using this technique, hIL13 mutants can be synthesized as a single polypeptide. Alternatively, shorter oligopeptide portions of the mutant hIL13 molecule can first be synthesized and then fused together to form the full length mutant by condensation of the amino terminus of one oligopeptide portion with the carboxyl terminus of the another oligopeptide portion to forming a peptide bond. The fusions can then be purified by standard protein chemistry techniques.

Mutants of hIL13 can also be produced through recombinant expression of hIL13-encoding nucleic acids (see below) in which the nucleic acid is modified, randomly or in a site-specific manner, to change (substitute), add to, or delete, some or all of the amino acids in the encoded polypeptide. Site-specific mutations can be introduced into the IL13-encoding nucleic acid by a variety of conventional techniques well described in the scientific and patent literature. Illustrative examples include: site-directed mutagenesis by overlap extension polymerase chain reaction (OE-PCR), as in Urban (1997) *Nucleic Acids Res.* 25: 2227–2228; Ke (1997) *Nucleic Acids Res.,* 25: 3371–3372, and Chattopadhyay (1997) *Biotechniques* 22: 1054–1056, describing PCR-based site-directed mutagenesis "megaprimer" method; Bohnsack (1997) *Mol. Biotechnol.* 7: 181–188; Ailenberg (1997) *Biotechniques* 22: 624–626, describing site-directed mutagenesis using a PCR-based staggered re-annealing method without restriction enzymes; Nicolas (1997) *Biotechniques* 22: 430–434, site-directed mutagenesis using long primer-unique site elimination and exonuclease III. Unique-site elimination mutagenesis can also be used (see, e.g., Dang et al. (1992) *Anal. Biochem.,* 200: 81). The production of mutants of biologically active proteins such as IFN-beta and IL-2 is described in detail in U.S. Pat. No. 4,853,332 and the mutation of hIL13 is described in Example 1 below.

Other hIL13 mutants can be prepared by chemically modifying native hIL13 according to known chemical modification methods. See, e.g., Belousov (1997) *Nucleic Acids Res.* 25:3440–3444; Frenkel (1995) *Free Radic. Biol. Med.* 19: 373–380; Blommers (1994) *Biochemistry* 33: 7886–7896. Likewise, hIL13 mutants made by chemical synthesis or by expression of nucleic acids as described above can be chemically modified to make additional hIL13 mutants.

Characterizing hIL13 Mutants

Mutants of hIL13 can have characteristics that differ from those native hIL13. For example, native hIL13 has the functional characteristics of binding both shared receptor and the restrictive receptor. Native hIL13 also has the characteristic of inducing transmembrane signals through binding shared receptors expressed on a cell surface. Such signaling can result in a measurable change in the cell's physiology. Changes can be the production of second messengers—e.g, an increase in intracellular [$Ca^{2+}$], activation of protein kinases and/or phosphorylases, changes in phosphorylation of a substrate, changes in signal transducers and activators of transcription, etc. They can also be changes in the cell proteome, e.g., from increased or decreased transcription or translation. Or they can be changes in a functional or phenotypic characteristic of the cell. For instance, adding native hIL13 to TF-1 cells can increase their rate of proliferation. As another example, adding native hIL13 can cause HUVEC to increase their expression of VCAM-1.

Characteristics of a given mutant hIL13 molecule can therefore be assessed by examining the ability of the molecule to bind the shared receptor and/or the restrictive receptor. Similarly, the ability of the mutant molecule to induce transmembrane signaling can be assessed by examining whether contacting a cell expressing an IL13 receptor with the mutant molecule results in a change in the cell's physiology. By these methods, hIL13 mutants can be characterized as those that bind both the shared receptor and/or the restrictive receptor, those that bind only one of the receptors, and those that do not bind either receptor. By quantifying the affinity of a mutant hIL13 molecule, it can also be characterized as one that binds with less, about equal, or more affinity than native hIL13. Mutants of hIL13 can also be characterized as having or lacking the ability to cause a transmembrane signal and/or a change in a cell's function or phenotype. The changes caused by a mutant hIL13 molecule can also be quantified to further characterize the molecule as one that causes such changes less than (of less magnitude), about equal to, or more than (of greater magnitude) those caused by native hIL13. For instance mutants of hIL13 that specifically bind to an hIL13 receptor associated with a cell in a manner that induces a measurable change in the cell's physiology can be those that modulate the proliferation rate of a cell line that expresses an IL13 receptor such as TF-1 cells. Antagonistic hIL13 mutants are those that reduce the proliferation rate of the cell line compared to that induced by native hIL13; agonistic hIL13 mutants are those that induce about same (e.g., 50–150% or 75–125% of) proliferation rate of the cell line as that induced by native hIL13; and superagonistic hIL13 mutants are those that increase the proliferation rate of the cell line compared to that induced by native hIL13. See Examples, below.

Chimeric Molecules of Mutant hIL13 and Effector Molecules

The invention also provides a chimeric molecule including a mutant hIL13 molecule conjugated to an effector molecule. The effector molecule can be any molecule that can be conjugated to an hIL13 mutant and exert a particular function. Examples of effector molecules include cytotoxins, drugs, detectable labels, targeting ligands, and delivery vehicles.

A mutant hIL13 molecule conjugated with a one or more cytoxins can be used to kill cells expressing a receptor to which the mutant binds. Cytotoxins for use in the invention can be any cytotoxic agent (i.e., molecule that can kill a cell after contacting the cell) that can be conjugated to hIL13 or an hIL13 mutant. Examples of cytotoxins include, without limitation, radionuclides (e.g., $^{35}S$, $^{14}C$, $^{32}P$, $^{125}I$, $^{131}I$, $^{90}Y$, $^{89}Zr$, $^{201}Tl$, $^{186}Re$, $^{188}Re$, $^{57}Cu$, $^{213}Bi$, $^{211}At$, etc.), conjugated radionuclides, and chemotherapeutic agents. Further examples of cytotoxins include, but are not limited to, antimetabolites (e.g., 5-flourouricil (5-FU), methotrexate (MTX), fludarabine, etc.), anti-microtubule agents (e.g., vincristine, vinblastine, colchicine, taxanes (such as paclitaxel and docetaxel), etc.), alkylating agents (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, tenoposide, and camptothecins), or other cytotoxic agents such as ricin, diptheria toxin (DT), Pseudomonas exotoxin (PE) A, PE40, abrin, saporin, pokeweed viral protein, ethidium bromide, glucocorticoid, and others. See, e.g. U.S. Pat. No. 5,932,188. Useful variations of PE and DT include PE38QQR (see, U.S. Pat. No. 5,614,191), PE1E and PE4E (see, e.g., Chaudhary et al. (1995) *J. Biol. Chem.,* 265:16306), and DT388 and DT398 (Chaudhary, et al. (1991) *Bioch. Biophys. Res. Comm.,* 180: 545–551) can also be used.

Mutant hIL13 molecules conjugated with one or more detectable labels can be used to detect the presence of a receptor to which the mutant binds, e.g., in diagnostic assays (e.g., in the detection of shed tumor cells overexpression the IL13 receptor) and/or in the in vivo localization of tumor cells. Detectable labels for use in the invention can be any substance that can be conjugated to hIL13 or an hIL13 mutant and detected. Suitable detectable labels are those that can be detected, for example, by spectroscopic, photochemical, biochemical, immunochemical, electrical, optical or chemical means. Useful detectable labels in the present invention include biotin or streptavidin, magnetic beads (e.g., Dynabeads™), fluorescent dyes (e.g., fluorescein isothiocyanate, texas red, rhodamine, green fluorescent protein, and the like), radiolabels (e.g., $^3$H, $^{125}$I, $^{35}$S, $^{14}$C, $^{32}$P, $^{111}$In, $^{97}$Ru, $^{67}$Ga, $^{68}$Ga, or $^{72}$As,), radioopaque substances such as metals for radioimaging, paramagnetic agents for magnetic resonance imaging, enzymes (e.g., horseradish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photo detector to detect emitted illumination. Enzymatic labels are typically detected by providing the enzyme with a substrate and detecting the reaction product produced by the action of the enzyme on the substrate, and colorimetric labels are detected by simply visualizing the colored label, and so forth.

Mutant hIL13 molecules conjugated with one or more targeting ligands (i.e., molecules that can bind a particular receptor) can be used to mediate binding of the mutants to a particular receptor or cell expressing the receptor. Any targeting ligand that can be conjugated to hIL13 or an hIL13 mutant can be used. Examples of such targeting ligands includes antibodies (or the antigen-binding portion of antibodies); and chemokines, growth factors, soluble cytokine receptors (e.g., those lacking a transmembrane domain), superantigens, or other molecules that bind a particular receptor. A large number of these molecules are known, e.g., IL-2, IL-4, IL-6, IL-7, tumor necrosis factor (TNF), anti-Tac, TGF-alpha., SEA, SEB, and the like. As a representative example, an hIL13 mutant can be conjugated with a soluble form of a hIL13 receptor. This conjugate, for example, could be used to both antagonize an endogenous hIL13 receptor on a cell and neutralize any hIL13 present in the vicinity of the cell.

Mutant hIL13 molecules conjugated with one or more nucleic acids can be used to specifically target delivery of the nucleic acid(s) to a target cell (e.g., one expressing an receptor to which the mutant binds). Any nucleic acid that can be conjugated to hIL13 or an hIL13 mutant can be used. The nucleic acids can be attached directly to the mutant hIL13, attached via a linker, or complexed with or encapsulated in another moiety (e.g., a lipid, a liposome, a viral coat, or the like) that is attached to the mutant IL13 molecule. The nucleic acid can provide any of number of effector functions. For example, a nucleic acid encoding one or more proteins can be used to deliver a particular enzymatic activity, substrate, and/or epitope to a target cell. For these applications or others where expression (e.g. transcription or translation) of the nucleic acid is desired, the nucleic acid is preferably a component of an expression cassette that includes all the regulatory sequences necessary to express the nucleic acid in the cell. Suitable expression cassettes typically include promoter initiation and termination codons, and are selected to optimize expression in the target cell. Methods of constructing suitable expression cassettes are well known to those of skill in the art. See, e.g., Sambrook et al., supra.

A mutant hIL13 molecule conjugated with a one or more drugs can be used to deliver such drug(s) to cells expressing a receptor to which the mutant binds. Any drug which can be conjugated to hIL13 or an hIL13 mutant can be used. Examples of such drugs include sensitizing agents that render a target (e.g., tumor) cell susceptible to various cancer therapeutics. The sensitizing agent can be a small molecule drug or a gene (under the control of a promoter in an appropriate expression cassette to induce expression in the target cell). For example, it has been proposed that expression of the herpes simplex virus (HSV) thymidine kinase (TK) gene in proliferating cells, renders the cells sensitive to the deoxynucleoside analog, ganciclovir. Moolten et at. (1986) *Cancer Res.* 46:5276–5281; Moolten et al. (1990) *Hum. Gene Ther.* 1: 125–134; Moolten et al. (1990) *J. Natl. Cancer Inst.* 82: 297–300; Short et al. (1990) *J. Neurosci. Res.* 27:427–433; Ezzedine et al. (1991) *New Biol.* 3: 608–614, Boviatsis et al. (1994) *Hum. Gene Ther.* 5: 183–191. HSV-TK mediates the phosphorylation of ganciclovir, which is incorporated into DNA strands during DNA replication (S-phase) in the cell cycle, leading to chain termination and cell death. Elion (1983) *Antimicr. Chemother.* 12, sup. B:9–17. A second example of a gene with a drug-conditional "killing" function is the bacterial cytosine deaminase gene, which confers chemosensitivity to the relatively non-toxic 5-fluorouracil precursor 5-fluorocytosine. Mullen et al. (1992) *Proc. Natl. Acad. Sci. USA* 89: 33–37; Huber et al. (1993) *Cancer Res.* 53: 4619–4626; Mullen et al. (1994) *Cancer Res.* 54: 1503–1506. Still another example of a gene with a drug-conditional "killing" function is a cytochrome P450 gene. Expression, of the gene product renders tumor cells sensitive to a chemotherapeutic agent, in particular, cyclophosphamide or ifosphamide. See, U.S. Pat. No. 5,688,773. The drug employed need not be a gene. For example, it can be one of the compounds that can treat multiple drug resistance of susceptible tumor cells described in U.S. Pat. No. 4,282,233. Other drugs can also be used. For example, chemotherapy drugs such as doxorubicin, vinblastine, genistein, and other described above can be conjugated to the mutant hIL13 molecule.

A mutant hIL13 molecule conjugated to a one or more delivery vehicles is also within the invention. Such conjugates can be used to deliver other substances such as a drug to cells expressing a receptor to which the mutant binds. Any delivery vehicle that can be conjugated to hIL13 or an hIL13 mutant can be used. Examples of such delivery vehicles include liposomes and lipids (e.g., micelles). Liposomes encapsulating drugs or micelles including drugs may also be used. Methods for preparing liposomes attached to proteins are well known to those of skill in the art. See, for example, U.S. Pat. No. 4,957,735; and Connor et al., *Pharm. Ther.,* 28: 341–365 (1985).

Effector molecules can be conjugated (e.g., covalently bonded) to a mutant hIL13 by any method known in the art for conjugating two such molecules together. For example, the mutant hIL13 can be chemically derivatized with an effector molecule either directly or using a linker (spacer). Several methods and reagents (e.g., cross-linkers) for mediating this conjugation are known. See, e.g., catalog of Pierce Chemical Company; and Means and Feeney, *Chemical Modification of Proteins,* Holden-Day Inc., San Francisco, Calif. 1971. Various procedures and linker molecules for attaching various compounds including radionuclide metal chelates, toxins, and drugs to proteins (e.g., to antibodies) are described, for example, in European Patent Application No. 188,256; U.S. Pat. Nos. 4,671,958; 4,659,839; 4,414, 148; 4,699,784; 4,680,338; 4,569,789; and 4,589,071; and Borlinghaus et al. *Cancer Res.* 47: 4071–4075 (1987). In particular, production of various immunotoxins is well-known within the art and can be found, for example in "Monoclonal Antibody—Toxin Conjugates: Aiming the Magic Bullet," Thorpe et al., *Monoclonal Antibodies in Clinical Medicine,* Academic Press, pp. 168–190 (1982); Waldmann (1991) *Science,* 252: 1657; and U.S. Pat. Nos. 4,545,985 and 4,894,443.

Where the effector molecule is a polypeptide, the chimeric molecule including the hIL13 mutant and the effector can be a fusion protein. Fusion proteins can be prepared using conventional techniques in molecular biology to join the two genes in frame into a single nucleic acid, and then expressing the nucleic acid in an appropriate host cell under conditions in which the fusion protein is produced.

A mutant hIL13 may be conjugated to one or more effector molecule(s) in various orientations. For example, the effector molecule may be joined to either the amino or carboxy termini of the mutant hIL13. The mutant IL13 molecule may also be joined to an internal region of the effector molecule, or conversely, the effector molecule may be joined to an internal location of the mutant IL13 molecule.

In some circumstances, it is desirable to free the effector molecule from the mutant hIL13 molecule when the chimeric molecule has reached its target site. Therefore, chimeric conjugates comprising linkages that are cleavable in the vicinity of the target site may be used when the effector is to be released at the target site. Cleaving of the linkage to release the effector molecule from the mutant IL13 molecule may be prompted by enzymatic activity or conditions to which the conjugate is subjected either inside the target cell or in the vicinity of the target site. When the target site is a tumor, a linker which is cleavable under conditions present at the tumor site (e.g. when exposed to tumor-associated enzymes or acidic pH) may be used. A number of different cleavable linkers are known to those of skill in the art. See, e.g., U.S. Pat. Nos. 4,618,492; 4,542,225; and 4,625,014. The mechanisms for release of an agent from these linker groups include, for example, irradiation of a photolabile bond and acid-catalyzed hydrolysis. U.S. Pat. No. 4,671, 958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given effector molecule to a mutant hIL13 molecule.

Nucleic Acids Encoding Mutant hIL13 Molecules and Methods of Making Mutant hIL13 Molecules Using Nucleic Acids The invention also provides purified nucleic acids encoding the mutant hIL13 molecules and the fusion proteins described above. Starting with a known protein sequence, DNA encoding the mutant hIL13 molecules or the fusion proteins may be prepared by any suitable method, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.,* 22: 1859–1862; and the solid support method of U.S. Pat. No. 4,458,066. Because of the degeneracy of the genetic code, a large number of different nucleic acids will encode the mutant hIL13 molecules and the fusion proteins. Each of these is included within the invention.

Chemical synthesis produces a single stranded oligonucleotide. This may be converted into double stranded DNA by hybridization with a complementary sequence, or by polymerization with a DNA polymerase using the single strand as a template. Longer DNA sequences may be obtained by the ligation of shorter sequences. Alternatively, subsequences may be cloned and the appropriate subsequences cleaved using appropriate restriction enzymes. The fragments may then be ligated to produce the desired DNA sequence.

DNA encoding the mutant hIL13 molecules or the fusion proteins may be cloned using DNA amplification methods such as polymerase chain reaction (PCR). Thus, in a preferred embodiment, the gene for hIL13 is PCR amplified, using primers that introduce one or more mutations. The primers preferably include restrictions sites, e.g., a sense primer containing the restriction site for NdeI and an anti-sense primer containing the restriction site for HindIII. In one embodiment, the primers are selected to amplify the nucleic acid starting at position 19, as described by McKenzie et al. (1987), supra. This produces a nucleic acid encoding the mature IL13 sequence (or mutant hIL13 molecules) and having terminal restriction sites.

For making DNA encoding the fusion proteins, the DNA encoding the effector molecule can be obtained from available sources. For example, the PE38QQR fragment may be excised from the plasmid pWDMH4-38QQR or plasmid pSGC242FdN1 as described by Debinski et al. *Int. J. Cancer,* 58: 744–748 (1994), and by Debinski et al. (1994) *Clin. Cancer Res.* 1:1015–1022 respectively. Ligation of the mutant IL13 molecule and a Pseudomonas exotoxin (e.g., PE38QQR) sequences and insertion into a vector produces a vector encoding the mutant IL13 joined to the terminus of the Pseudomonas exotoxin (e.g., joined to the amino terminus of PE38QQR, PE1E, or PE4E (position 253)). In a preferred embodiment, the two molecules are joined directly. Alternatively there can be an intervening peptide linker (e.g., a three amino acid junction consisting of glutamic acid, alanine, and phenylalanine introduced by the restriction site).

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the solubility, folding, net charge, or hydrophobicity.

The nucleic acid sequences encoding the mutant hIL13 molecules or the fusion proteins may be expressed in a variety of host cells, including *E. coli,* other bacterial hosts, yeast, and various higher eukaryotic cells such as the COS, CHO and HeLa cells lines and myeloma cell lines. The recombinant protein gene will be operably linked to appropriate expression control sequences for each host. F or *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV 40, cytomegalovirus, etc., and a polyadenylation sequence, and may include splice donor and acceptor sequences.

Plasmid vectors of the invention made as described above can be transferred into the chosen host cell by well-known methods such as calcium chloride, or heat shock, transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant mutant hIL13 molecules or fusion proteins can be purified according to standard procedures of the art, including ammonium sulfate precipitation, affinity columns, column chromatography, gel electrophoresis and the like. See, generally, R. Scopes, *Protein Purification,* Springer-Verlag, N.Y. (1982); and Deutscher, *Methods in Enzymology Vol.* 182: *Guide to Protein Purification,* Academic Press, Inc. N.Y. (1990). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

After chemical synthesis, biological expression, or purification, the mutant hIL13 molecules or the fusion proteins may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art. See, Debinski et al. (1993) *J. Biol. Chem.,* 268: 14065–14070; Kreitman and Pastan (1993) *Bioconjug. Chem.,* 4: 581–585; and Buchner, et al. (1992) *Anal. Biochem.,* 205: 263–270.

Modifications can be made to the IL13 receptor targeted fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Antibodies

Mutants of hIL13 (or immunogenic fragments or analogs thereof) can be used to raise antibodies useful in the invention. Such polypeptides can be produced by recombinant techniques or synthesized as described above. In general, hIL13 mutants can be coupled to a carrier protein, such as KLH, as described in Ausubel et al., supra, mixed with an adjuvant, and injected into a host mammal. Antibodies produced in that animal can then be purified by peptide antigen affinity chromatography. In particular, various host animals can be immunized by injection with an hIL13 mutant or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Other potentially useful adjuvants include BCG (bacille Calmette-Guerin) and Corynebacterium parvum.

Polyclonal antibodies are heterogeneous populations of antibody molecules that are contained in the sera of the immunized animals. Antibodies within the invention therefore include polyclonal antibodies and, in addition, monoclonal antibodies, single chain antibodies, Fab fragments, F(ab')$_2$ fragments, and molecules produced using a Fab expression library. Monoclonal antibodies, which are homogeneous populations of antibodies to a particular antigen, can be prepared using the mutants of hIL13 described above and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Once produced, polyclonal or monoclonal antibodies can be tested for specific recognition of the mutants by Western blot or immunoprecipitation analysis by standard methods, for example, as described in Ausubel et al., supra. Antibodies that specifically recognize and bind to hIL13 mutants are useful in the invention. For example, such antibodies can be used to monitor the amount of an hIL13 mutant associated with a cell or to block binding of a particular mutant a receptor.

Antibodies of the invention can be produced using fragments of the hIL13 mutants that lie outside highly conserved regions and appear likely to be antigenic, by criteria such as high frequency of charged residues. Cross-reactive anti-hIL13 mutant antibodies are produced using a fragment of a hIL13 mutant that is conserved amongst members of this family of proteins. In one specific example, such fragments are generated by standard techniques of PCR, and are then cloned into the pGEX expression vector (Ausubel et al., supra). Fusion proteins are expressed in *E.coli* and purified using a glutathione agarose affinity matrix as described in Ausubel, et al., supra. Non-cross reactive antibodies can be prepared by adsorbing the antibody with the antigen(s) that the antibody is desired not to react with. For example, antisera prepared against a particular hIL13 mutant can be adsorbed with other hIL13 mutants and/or native hIL13 to reduce or eliminate cross-reactivity.

In some cases it may be desirable to minimize the potential problems of low affinity or specificity of antisera.

In such circumstances, two or three fusions can be generated for each protein, and each fusion can be injected into at least two rabbits. Antisera can be raised by injections in a series, preferably including at least three booster injections. Antiserum is also checked for its ability to immunoprecipitate recombinant mutants of hIL13 or control proteins, such as glucocorticoid receptor, CAT, or luciferase.

Techniques described for the production of single chain antibodies (U.S. Pat. Nos. 4,946,778, 4,946,778, and 4,704, 692) can be adapted to produce single chain antibodies against an hIL13 mutant, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science 246:1275, 1989) to allow rapid and easy identification of monoclonal Fab fragments with the desired specificity.

The antibodies of the invention can be used, for example, in the detection of a hIL13 mutant in a biological sample. Antibodies can also be used to interfere with the interaction of an hIL13 mutant and other molecules that bind the mutant (e.g., an hIL13 receptor).

Methods of Delivering a Mutant hIL13 Molecule to a Cell

The invention also provides a method of delivering an IL13 mutant to a cell. This method is useful, among other things, for directing a chimeric molecule including the hIL13 mutant and an effector molecule to a cell so that the effector molecule can exert its function. For example, an hIL13 mutant conjugated to a cytotoxin can be delivered to a target cell to be killed by mixing a composition containing the chimeric molecule with the target cell expressing a receptor that binds the mutant. As another example, an hIL13 mutant conjugated to a detectable label can be directed to a target cell to be labeled by mixing a composition containing the chimeric molecule with the target cell expressing a receptor that binds the mutant.

Mutant hIL13 molecules can be delivered to a cell by any known method. For example, a composition containing the hIL13 mutant can be added to cells suspended in medium. Alternatively, a mutant hIL13 can be administered to an animal (e.g., by a parenteral route) having a cell expressing a receptor that binds the mutant so that the mutant binds to the cell in situ. The mutant ILI3 molecules of this invention are particularly well suited as targeting moieties for binding tumor cells because tumor cells overexpress ILI3 receptors. In particular, carcinoma tumor cells (e.g. renal carcinoma cells) overexpress ILI3 receptors at levels ranging from about 2100 sites/cell to greater than 150,000 sites per cell. Similarly, gliomas and other transformed cells also overexpress ILI3 receptors (ILI3R). Thus, the methods of this invention can be used to target an effector molecule to a variety of cancers. Such cancers are well known to those of skill in the art and include, but are not limited to, cancers of the skin (e.g., basal or squamous cell carcinoma, melanoma, Kaposi's sarcoma, etc.), cancers of the reproductive system (e.g., testicular, ovarian, cervical), cancers of the gastrointestinal tract (e.g., stomach, small intestine, large intestine, colorectal, etc.), cancers of the mouth and throat (e.g. esophageal, larynx, oropharynx, nasopharynx, oral, etc.), cancers of the head and neck, bone cancers, breast cancers, liver cancers, prostate cancers (e.g., prostate carcinoma), thyroid cancers, heart cancers, retinal cancers (e.g., melanoma), kidney cancers, lung cancers (e.g., mesothelioma), pancreatic cancers, brain cancers (e.g. gliomas, medulloblastomas, meningiomas, etc.) and cancers of the lymph system (e.g. lymphoma). In a particularly preferred embodiment, the methods of this invention are used to target effector molecules to brain cancers (especially gliomas).

One of skill in the art will appreciate that identification and confirmation of ILI3 overexpression by other cells requires only routine screening using well-known methods. Typically this involves providing a labeled molecule that specifically binds to the ILI3 receptor (e.g., a native or mutant ILI3). The cells in question are then contacted with this molecule and washed. Quantifying the amount of label remaining associated with the test cell provides a measure of the amount of ILI3 receptor (ILI3R) present on the surface of that cell. In a preferred embodiment, IL13 receptor may be quantified by measuring the binding of $^{125}$I-labeled IL13 ($^{125}$I-ILI3) to the cell in question. Details of such a binding assay are provided in U.S. Pat. No. 5,614,191.

As IL13 has been implicated in playing an important regulatory role in allergic hyperactivity reactions such as asthma (Webb et al. (2000) J. Immunol. 165:108–113), the invention also provides a method of modulating an allergic response by contacting a cell important in the response (e.g., a lymphocyte such as a B cell, an eosinophil, a mast cell, and/or any other cells involved in Th$_2$-dominated inflammatory responses) with one or more hIL13 mutants. Thus, for example, where interaction of native hIL13 with an hIL13 receptor expressed on a cell causes transmembrane signals that contribute to the cell's role in an allergic reaction (e.g., inducing inflammation), a mutant hIL13 can be used to block this interaction and inhibit the allergic reaction. The interaction between native hIL13 and the IL13 receptor can be blocked, for example, by contacting the cell 1 can with an hIL13 mutant that binds to the IL13 receptor (in some cases with more affinity than native hIL13) but does not cause the transmembrane signaling through the receptor. For asthma, such an hIL13 mutant could be administered by inhalation of a pharmaceutical composition containing the mutant.

Pharmaceutical Compositions

The mutant hIL13 molecules (including those conjugated with an effector molcule) of this invention can be prepared for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It some cases it may be desirable to protect the fusion proteins and pharmaceutical compositions of this invention, from being digested (e.g., when administered orally). This can be accomplished either by complexing the protein with a composition that renders it resistant to acidic and enzymatic hydrolysis, or by packaging the protein in an appropriately resistant carrier such as a liposome. Means of protecting compounds from digestion are well known in the art (see, e.g., U.S. Pat. No. 5,391,377 describing lipid compositions for oral delivery of therapeutic agents).

The pharmaceutical compositions can also be delivered to an animal by inhalation by any presently known suitable technique. For example, the hIL13 mutants of the invention can be delivered in the form of an aerosol spray produced from pressurized packs or a nebulizer, with the use of a suitable propellant such as dichlorodifluromethane, trichlorotrifluoromethane, dichlorotetrafluorethane, carbon dioxide, or any other suitable gas. In the case of a pressurized aerosol, the dosage unit may be controlled using a valve to deliver a metered amount. Capsules and cartridges (e.g., of gelatin) containing a powder mix of the hIL13 mutant and a suitable base (e.g., lactose or starch) can be used in an inhaler or insufflator to deliver the mutant to the respiratory tract of an animal.

The pharmaceutical compositions of this invention are particularly useful for parenteral administration, such as intravenous administration or administration into a body cavity or lumen of an organ. The compositions for administration will commonly comprise a solution of the mutant hIL13 molecule dissolved in a pharmaceutically acceptable carrier, preferably an aqueous carrier. A variety of aqueous carriers can be used, e.g., buffered saline and the like. These solutions are sterile and generally free of undesirable matter (e.g., pyrogens). These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the mutant hIL13 in these formulations can vary widely, and will be selected primarily based on fluid volumes, viscosities, body weight and the like in accordance with the particular mode of administration selected and the patient's needs. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

Toxicity and therapeutic efficacy of the pharmaceutical compositions utilized in the invention can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Doses that exhibit large therapeutic indices are preferred. While those that exhibit toxic side effects may be used, care should be taken to design a delivery system that targets the pharmaceutical composition to the site of affected tissue in order to minimize potential damage to uninfected cells and, thereby, reduce side effects.

The data obtained from cell culture assays and animal studies can be used in formulating a range of dosage for use in humans. The dosage of such pharmaceutical compositions lies preferably within a range of circulating concentrations that include an $ED_{50}$ with little or no toxicity. The dosage may vary within this range depending upon the dosage form employed and the route of administration utilized. For any pharmaceutical composition used in a method of the invention, the therapeutically effective dose can be estimated initially from cell culture assays. A dose can be formulated in animal models to achieve an $IC_{50}$ (that is, the concentration of the test compound which achieves a half-maximal inhibition of symptoms) as determined in cell culture. Such information can be used to more accurately determine useful doses in humans. Levels in plasma can be measured, for example, by high performance liquid chromatography. Although dosage should be determined for each particular application, it is expected that a dose of a typical pharmaceutical composition for intravenous administration would be about 0.1 to 10 mg per patient per day. Dosages from 0.1 up to about 100 mg per patient per day may be used, particularly when the pharmaceutical compositions is administered to a secluded site and not into the blood stream, such as into a body cavity or into a lumen of an organ.

The compositions containing the present hIL13 mutants, or a cocktail thereof (i.e., with other proteins), can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the proteins of this invention to effectively treat the patient.

Among various uses of the cytotoxic fusion proteins of the present invention are included a variety of disease conditions caused by specific human cells that may be eliminated by the toxic action of the protein. One preferred application is the treatment of cancer (e.g., a glioma), such as by the use of an mutant IL13 ligand attached to a cytotoxin (e.g., PE or a PE derivative).

It will be appreciated by one of skill in the art that there are some regions that are not heavily vascularized or that are protected by cells joined by tight junctions and/or active transport mechanisms which reduce or prevent the entry of macromolecules present in the blood stream. For example, systemic administration of therapeutics to treat gliomas, or other brain cancers, is constrained by the blood-brain barrier which resists the entry of macro-molecules into the subarachnoid space. Thus, the therapeutic compositions of this invention can be administered directly to the tumor site. For instance, brain tumors (e.g., gliomas) can be treated by administering the therapeutic composition directly to the tumor site (e.g., through a surgically implanted catheter). Where the fluid delivery through the catheter is pressurized, small molecules (e.g. the therapeutic molecules of this invention) will typically infiltrate as much as two to three centimeters beyond the tumor margin.

Alternatively, the therapeutic composition can be placed at the target site in a slow release formulation (e.g., a thrombin-fibrinogen mixture). Such formulations can include, for example, a biocompatible sponge or other inert or resorbable matrix material impregnated with the therapeutic composition, slow dissolving time release capsules or microcapsules, and the like.

Typically the catheter, or catheters, or time release formulation will be placed at the tumor site as part of a surgical procedure. Thus, for example, where major tumor mass is surgically debulked, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

Imaging

The invention also provides a method of imaging a cell expressing a receptor that binds an hIL13 mutant in vivo. In an exemplary method, an hIL13 mutant conjugated to a label detectable by the chosen imaging technique is administered to an animal having the cell expressing a receptor that binds the particular hIL13 mutant. The animal is then imaged using the chosen imaging technique. Examples of labels useful for diagnostic imaging include radiolabels such as $^{131}$I, $^{111}$In, $^{123}$I, $^{99m}$Tc, $^{32}$P, $^{125}$I, $^{3}$H, $^{14}$C, and $^{188}$Rh; fluorescent labels such as fluorescein and rhodamine; nuclear magnetic resonance active labels; positron emitting isotopes detectable by a positron emission tomography ("PET") scanner; chemiluminescent labels such as luciferin; and enzymatic markers such as peroxidase or phosphatase. Mutants of hIL13 can be labeled with such reagents as described above or using techniques known in the art.

Any imaging technique compatible with the labeled-hIL13 mutant can be used. Examples of such techniques include immunoscintigraphy where a gamma camera is used to detect the location and distribution of gamma-emitting radioisotopes; MRI where a paramagnetic labeled-hIL13 mutant is used; PET where an hIL13 mutant is conjugated with a positron emitting label; and X-ray imaging where an hIL13 mutant is conjugated with a radioopaque label (e.g., a metal particle). A more detailed description of such techniques is provided in *Handbook of Targeted Delivery of Imaging Agents* (*Handbook of Pharmacology and Toxicology*), ed. V. Torchilin, CRC Press, 1995; Armstrong et al., *Diagnostic Imaging,* Blackwell Science Inc., 1998; and *Diagnostic Nuclear Medicine,* ed. C. Schiepers, Springer Verlag, 2000.

As an illustrative example, the location of glioma tumor cells in an animal can be determined by injecting (e.g., parenterally or in situ) an animal with a composition including native hIL13 or an hIL13 mutant conjugated to a detectable label (e.g., a gamma emitting radioisotope). The composition is then allowed to equilibrate in the animal, and to bind to the glioma cells. The animal is then subjected to imaging (e.g., using a gamma camera) to image where the glioma cells are.

Diagnostic Kits

In another embodiment, this invention provides for kits for the treatment of tumors or for the detection of cells overexpressing IL13 receptors. Kits will typically comprise a chimeric molecule of the present invention (e.g., a mutant hIL13 conjugated to a detectable label, a mutant hIL13 conjugated to cytotoxin, a mutant IL13 conjugated to a targeting ligand, etc.). In addition the kits will typically include instructional materials disclosing means of use of chimeric molecule (e.g., as a cytotoxin, for detection of tumor cells, to augment an immune response, etc.). The kits may also include additional components to facilitate the particular application for which the kit is designed. Thus, for example, where a kit contains a chimeric molecule in which the effector molecule is a detectable label, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

EXAMPLES

The present invention is further illustrated by the following specific examples. The examples are provided for illustration only and are not to be construed as limiting the scope or content of the invention in any way.

Example 1

Materials and Methods

Restriction endonucleases and DNA ligase were obtained from New England Biolabs (Beverly, Mass.), Bethesda Research Laboratories (BRL, Gaithersburg, Md.) and Boehringer Mannheim (Indianapolis, Ind.). U.S.E. mutagenesis kit, fast protein liquid chromatographic (FPLC) system, columns and media were obtained from Pharmacia (Piscataway, N.J.). Oligonucleotide primers were synthesized at the Macromolecular Core Laboratory, Penn State College of Medicine. Polymerase chain reaction (PCR) kit was from Perkin-Elmer Cetus (Norwalk, Conn.). Tissue culture ware was from Corning (Corning, N.Y.). 3-(4,5-dimethylthiazol-2-yl)-5-(3-carboxymethoxyphenyl)-2-(4-sulfophenyl)-2H-tetrazolium (inner salt)/phenazine methasulfate (MTS/PMS) non-radioactive cell proliferation assay was purchased from Promega (Madison, Wis.). SDS-PAGE supplies were from BioRad (Hercules, Calif.). Antibodies were purchased from Santa Cruz Biotechnology (Santa Cruz, Calif.). SuperSignal Substrate for chemiluminescent detection was purchased from Pierce (Rockford, Ill.). Cell lines were obtained from the American Type Culture Collection (Rockville, Md.). MTS/PMS for cell titer 96 aqueous non-radioactive cell proliferation assay was purchased from Promega (Madison, Wis.).

For recombinant protein expression in a prokaryotic system, all plasmids carrying the genes encoding proteins of interest were under a T7 promoter-based expression system. The plasmids were constructed as described in Debinski et al., (1998) Nature Biotech., 16:449–453. BL21(IDE3) *E. coli,* which carry the T7 RNA polymerase gene in an isopropyl-1-thio-b-galactopyranoside (IPTG) inducible form, were used as the host for recombinant protein expression. Production of recombinant proteins driven by T7 RNA polymerase allowed production of milligram quantities of recombinant protein from a 1.0 liter culture induced at $A_{600}$ of 2.0.

For expression of proteins, competent BL21 cells were transformed with the appropriate plasmids and grown in Terrific Broth (DIFCO Laboratories, Detroit Mich.) to $A_{600}$ equal to 2.0, at which point IPTG was added to a final concentration of 250 mM. Cells were harvested 90 min. later. The inclusion body fraction of the cells was isolated and denatured in 7M guanidine HCl, then renatured by rapid dilution into buffer, using the disulfide-shuffling method as was previously described in Debinski et al. (1993) J. Biol. Chem., 268:14065–14070. After dialysis, the renatured proteins were purified using a Pharmacia fast protein liquid chromatography (FPLC) system.

For mutagenesis, mutations of the hIL13 gene were made by standard PCR protocols (using the mutated oligonucleotides as sense or anti-sense primers in PCR) or by using a unique site elimination (U.S.E.) mutagenesis kit, based on the procedure developed by Deng and Nickoloff in Anal. Biochem., 200:81–88, 1992. All mutated plasmids were isolated and sequenced to verify the correct mutation prior to use.

For polyacrylamide gel electrophoresis and immunoblotting, the purity of the isolated recombinant proteins was determined by sodium dodecyl sulfate polyacrylamide gel electrophoresis, under nonreducing conditions. The separated proteins in the gel were stained either with Coomassie Blue for visual inspection or transferred to polyvinylidene difluoride (PVDF) membrane for Western blot analysis. For Western blot analysis, the PVDF with the transferred proteins was incubated in 5% nonfat milk in phosphate buffered saline (PBS) for one hour at room temperature. The membrane was incubated for one hour in 5% milk/PBS containing goat anti-human IL13 antibody (1:1,000 dilution). The antibody was raised against a hIL13 specific peptide located at the carboxy terminus of hIL13. After incubation with the primary antibody, the membrane was washed three times, five min. each, with 0.05% Tween 20/PBS. The membrane was then incubated for one hour in 5% milk/PBS containing donkey anti-goat IgG conjugated with horseradish peroxidase (1:20,000 dilution). The membrane was washed three times, five min. each, with 0.05% Tween 20/PBS. The immuno-reactive proteins were identified on film, using enhanced chemiluminescence detection. Images were digitized using a Hewlett Packard Scan-Jet 6100C scanner and composited using Microsoft Powerpoint software.

For circular dichroism (CD), CD spectra for the proteins were obtained over the wavelength range of 185–260 nm using a Jasco J-710 spectropolarimeter. All measurements were carried at 37° C., using the same cuvette, the same orientation of the cuvette to the light source, and a 2 mm light path. Proteins (0.1 mg/ml) were resuspended in phosphate buffered saline (PBS) and then analyzed. For unfolded samples, protein was resuspended in 8M urea containing 40 mM DTT (denaturation buffer). Reported spectra were the average of three consecutive runs for each sample. Spectra from appropriate blanks, PBS alone or denaturation buffer, were subtracted from each sample so that the resulting spectra reflected only the CD contribution of the proteins.

For cell proliferation assays, cell killing by cytotoxins was tested as follows. $5 \times 10^3$ cells per well were plated in a 96-well tissue culture plate in 150 ml of media. Various concentrations of cytotoxins were diluted in 0.1% BSA/PBS and 25 ml of each dilution was added to cells 18–24 h following cell plating. Cells were incubated at 37° C. for another 48 h. Then, the cytotoxicity was determined using a colorimetric MTS [3-(4,5-dimethylthiazol-2-yl)-5-(3-carboxymethoxyphenyl)-2-(4-sulfophenyl)-2H-tetrazolium, inner salt]/PMS (phenazine methasulfate) cell proliferation assay. MTS/PMS was added at a half final concentration as recommended by the manufacturer. The cells were incubated with the dye for 4 hr and then the absorbance was measured at 490 nm for each well using a micro-plate reader (Cambridge Technology, Inc., Watertown, Mass.). The wells containing cells treated with cycloheximide (10 mM) or wells with no viable cells left served as a background for the assay. For blocking studies, interleukins at a concetration of 1.0 ug/ml were added to cells for 60 min before the cytotoxins addition.

Cell proliferation studies using TF-1 cells (pre-leukemic human B cells, which express the shared IL13/4 receptor) were performed by growing the cells in the presence of different concentrations of wild-type interleukins or their mutants in 96 well culture plates. After 72 h of incubation at 37° C., the rate of proliferation of the TF-1 cells was determined by a colorimetric MTS [3-(4,5-dimethylthiazol-2-yl)-5-(3-carboxymethoxyphenyl)-2-(4-sulfophenyl)-2H-tetrazolium, inner salt]/PMS (phenazine methasulfate) cell proliferation assay. The cell samples were incubated with the dye for four h then their absorbance at 490 nm was recorded for each well using a microplate reader. The wells with cells treated with high concentrations of cycloheximide served as background for the assay.

For indirect immunofluorescence analyses, HUVEC were seeded onto an eight chambered slide, 50,000 cells per chamber, and incubated overnight at 37° C. to allow cells to attach. The media was removed and replaced with media containing hIL13 or its mutants (1 mg/ml final concentration). The cells were incubated again overnight at 37° C. The next day, the media was removed, the cells were fixed in ethanol and incubated with blocking media (10% normal rabbit serum in PBS) at room temperature for 20 min. The blocking media was removed and goat anti-VCAM-1 antibody (1 ug/ml) in 1.5% normal rabbit serum/PBS was added. Cells were incubated at room temperature for one hour, then primary antibody was removed and cells rinsed three times, five min. each, with PBS. Cells were incubated with rabbit anti-goat IgG-Cy3 conjugate (1:150 dilution) in 1.5% normal rabbit serum/PBS for 45 min. at room temperature, in the dark. After 45 min., the cells were rinsed three times, five min. each, with PBS, a coverslip was mounted using aqueous mounting medium, and the fluorescent staining determined using a rhodamine filter set. Images were obtained from the same experiment without adjusting the microscope between samples on a Zeiss Axioplan microscope and captured digitally using Snappy by Play Inc.

For cytotoxicity-blocking assays, glioblastoma cells (U-251 MG and SNB-19) were plated into 96-well culture plates and incubated for 24 h. After 24 h, hIL13 or its mutants were added to cells and incubated for one hour at 37° C. An equal volume of 0.1% BSA in PBS was added to cells for assays without blocking ligand. After the hour incubation, increasing concentration of the hIL13 chimeric toxin (hIL13-PE1E; see Debinski, et al. (1996) J. Biol. Chem., 271, 22428–22433)) was added (0.001–10 ng/ml final concentration) and the cells were incubated for three days. After three days, the number of proliferating cells in each well was determined using the colorimetric MTS/PMS method described above. The wells with cells treated with high concentrations of cycloheximide served as background for the assay.

For autoradiography, recombinant hIL13.E13Y was iodolabeled with $^{125}$I by using the IODO-GEN® (Pierce Biotechnology Rockford, Ill.) reagent (1,3,4,6-tetrachloro-3α-6α-diphenylglycouril) according to the manufacturer's instructions. The specific activity of $^{125}$I-hIL13.E13Y was ~300 mCi/mg of protein. All studies involving human specimens were approved by the respective Human Subjects Protection Offices at the Penn State College of Medicine (Protocol No. IRB 96-123EP). Serial tissue sections were cut (10 mm) on a cryostat, thaw-mounchrome alumme-alum coated slides, and stored at 4° C. until analyzed. To observe binding distribution of $^{125}$I-hIL13.E13Y, sections were incubated (1 hr, 22° C.) with 1.0 nM $^{125}$I-hIL13 in binding buffer (200 mM sucrose, 50 mM HEPES, 1% BSA, 10 mM EDTA). Adjacent serial sections were incubated with the radiolabeled recombinant hIL13.E13Y after a 30 min preincubation at 22° C. in the presence of binding buffer alone or of a 100- to 500-fold molar excess of unlabeled hIL13, hIL13.E13Y or hIL4, or a monoclonal antibody against human transferrin receptor (TfR). To dissociate non-specifically bound radioligand, sections were rinsed in four consecutive changes (5 minutes each) of ice-cold 0.1 M PBS. At least two sections of each of the tissue specimens were assayed for the evaluation of $^{125}$I-hIL13.E13Y binding specificity. After drying, labeled sections were apposed to Kodak autoradiography film at –65° C. for 8 hr to 11 days.

Example 2

Radioimmunodetection and Radioimmunotherapy of Human High Grade Gliomas

The IL13 mutein, hIL13.E13Y, was prepared as described above and tested for its ability to modulate the interleukin-induced proliferative responses of TF-1 cells. TF-1 cells were treated with hIL13, hIL13.E13Y, or hIL13.E13K. While hIL13 was very potent in stimulating the growth of TF-1 cells, hIL13.E13K showed no activity and hIL13.E13Y exhibited only very weak activity, if any at all.

The ability of hIL13.E13Y to compete for the hIL13 binding sites in clinical specimens of glioblastoma (GBM) in situ was investigated in autoradiographic studies. The two GBM tissues studied labeled densely with $^{125}$I-hIL13.E13Y binding sites, as well as with labeled wild type hIL13. The binding was specific since both hIL13.E13Y and the wild type IL13 blocked the binding of $^{125}$I-hIL13.E13Y. In contrast, an excess of recombinant hIL4 was largely without influence on the $^{125}$I-hIL13.E13Y binding to GBM specimens.

In another test of specificity of the hIL13.E13Y binding to GBM, the ability of a monoclonal antibody against the transferrin receptor (TfR) to displace the binding of radiolabeled interleukin was examined. No cross-competition for the hIL13 binding sites in the GBMs examined was observed. The binding of hIL13.E13Y to GBM appears to be very specific as others studies have shown that $^{125}$I-hIL13 fails to interact with normal brain or normal human cells and that $^{125}$I-hIL13.E13Y does not interact with normal human cells, such as HUVEC.

In other tests, the ability of hIL13.E13Y to block the action of hIL13-PE1E (an hIL13-based cytotoxin) was investigated using two different human malignant glioma cell lines. Glioma cells in culture were pretreated with either hIL13, hIL13.E13Y or hIL13.E13K before hIL13-PE1E was added. The cytotoxicity of hIL13-PE1E was neutralized in these cultures using hIL13, hIL13.E13Y, or hIL13.E13K.

Example 3

Figure 1A:
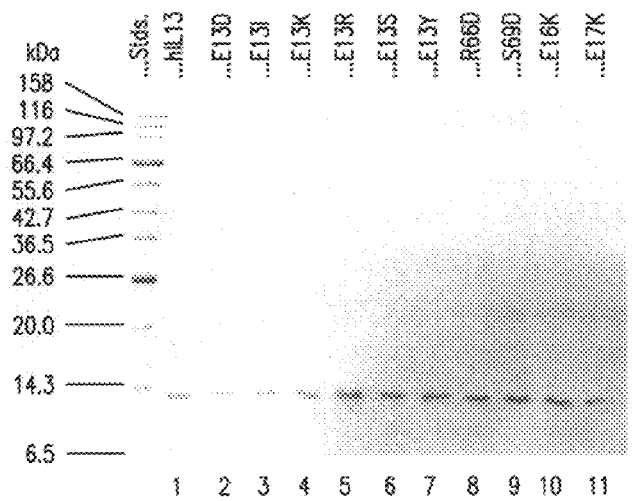
Figure 1B:
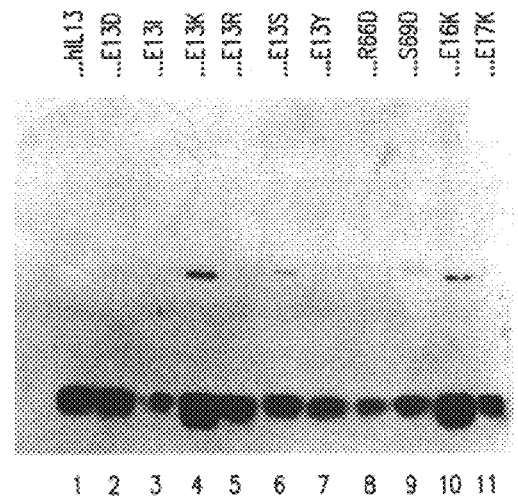
Figure 2A:
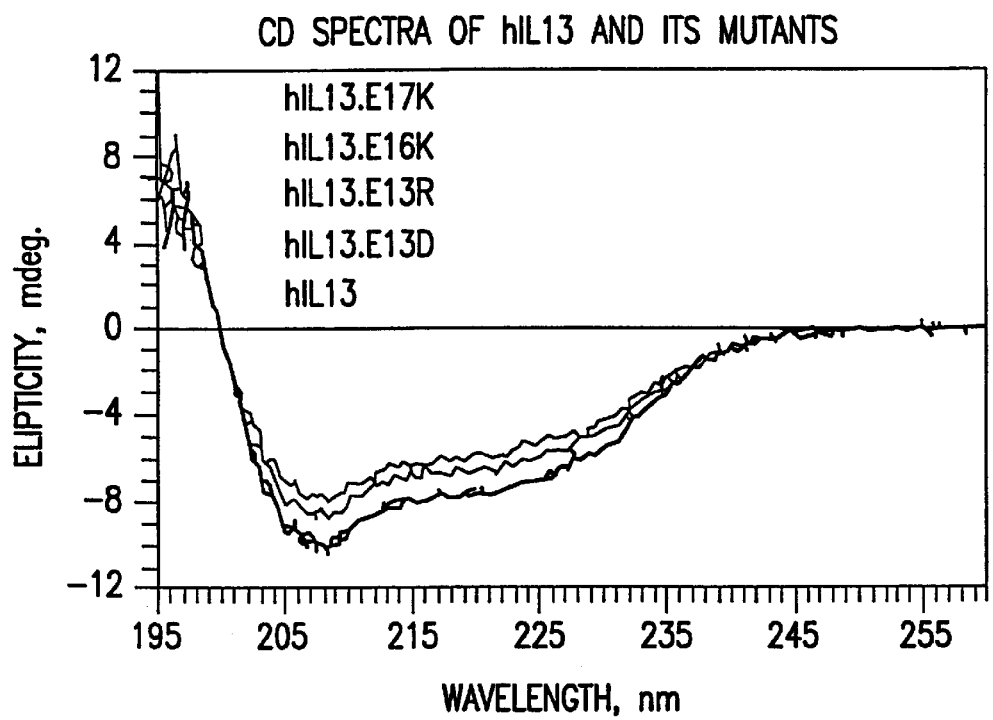
Figure 2B:
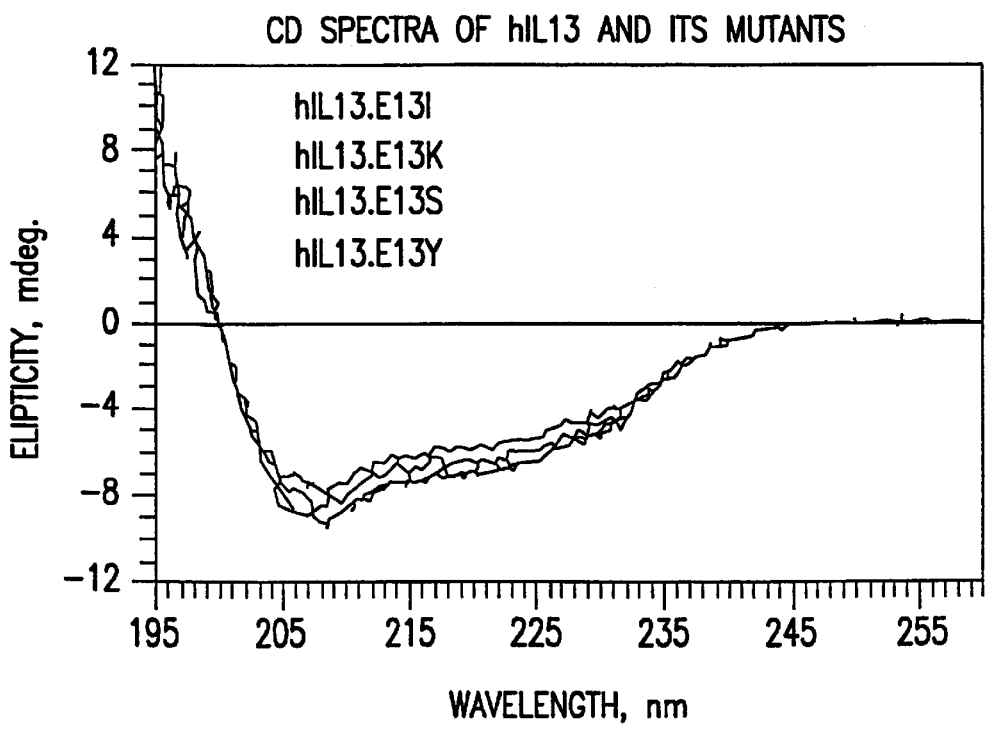
Figure 2C:
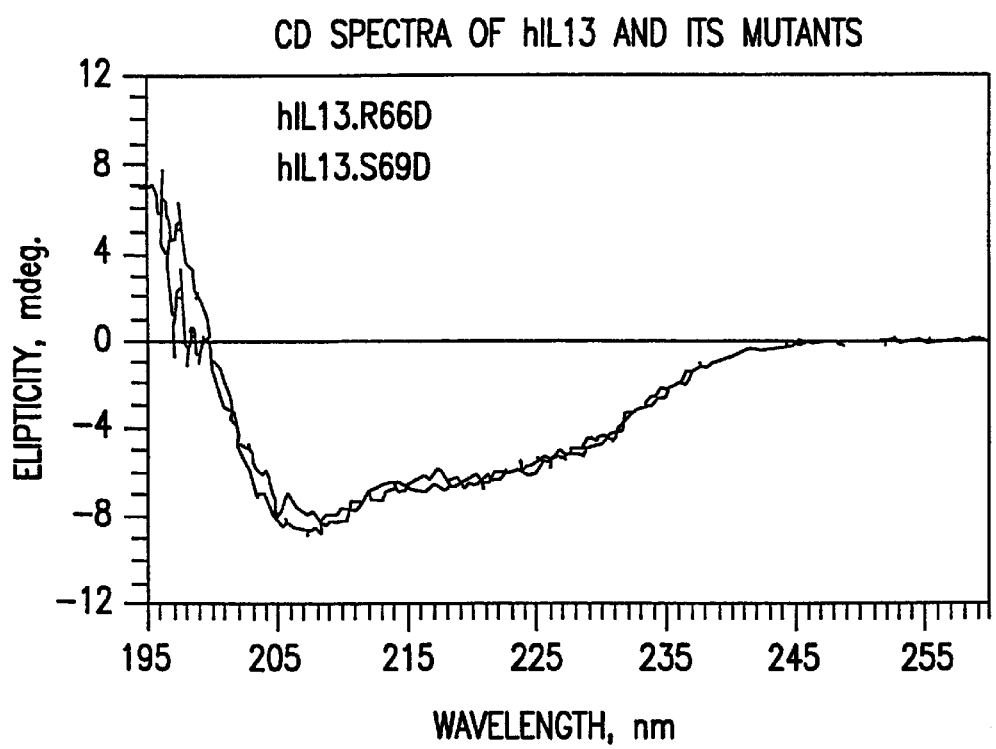
Figure 2D:
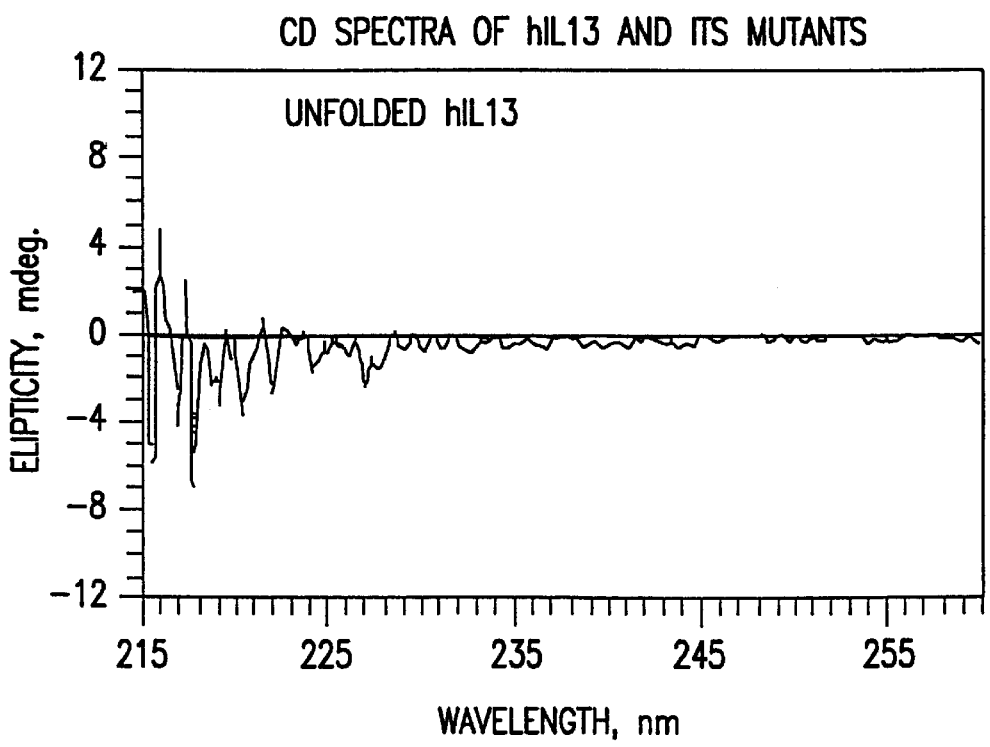

Mutants of Interleukin 13 with Altered Reactivity Towards Interleukin 13 Receptors Recombinant IL-13 and IL-13 mutants were prepared, isolated, and purified as described in Example 1. The prokaryotic production of the cytokines or their mutants under control of the T7 promoter was very efficient. After purification, between 0.5 mg and 1.5 mg of each cytokine or mutant was obtained from a 1 liter culture. When each purified protein was analyzed using SDS-PAGE and stained with Coomassie Blue, a single protein band was observed migrating at approximately 13 kDa (FIG. 1, panel A). Visual inspection suggested that all preparations were greater than 95% pure. A corresponding Western blot of the samples using a goat polyclonal anti-hIL13 antibody (that was not cross-reactivity with any other cytokine) indicated that the isolated proteins were immuno-reactive with hIL13 (FIG. 1, panel B). The alpha-helix D mutants, hIL13.R109D and hIL13.F113D, also reacted with this antibody indicating that they too were immuno-reactive with hIL13 (data not shown). Traces of a dimeric form (~26 kDa) of some of the mutated cytokines were also detected.

To determine whether the recombinant interleukins had refolded correctly and that their mutation had not destroyed their general pattern of conformation, circular dichroism (CD) was used to determine the proteins' folded structure. The secondary structure data from the spectropolarimeter indicated that each protein sample produced a spectrum consistent with an alpha-helical enriched protein, having two spectral minima at approximately 208 nm and 222 nm (FIG. 2). Furthermore, the CD spectrum of each mutant could be superimposed on the CD spectrum of the wild-type hIL13, although slight variations in spectra intensity were observed between samples (FIG. 2, panels A, B, C). hIL13.R109D and hIL13.F113D both produced CD spectra similar to the other mutants (not shown). For comparison, the CD spectrum of unfolded hIL13 was also obtained (FIG. 2, panel D). The panel illustrates the collapse of the characteristic alpha-helical pattern when the protein is unfolded.

Functional assays were employed to examine whether the IL13 mutants exhibited an altered association with the shared signaling IL13/4 receptor by measuring their effect on induced TF-1 cell proliferation. TF-1 cells express the shared IL13/4 receptor (but not the restricted receptor) and proliferate in a dose-dependent manner in the presence of hIL 13 or hIL4. Under the conditions used in this assay, a concentration of 100 ng/ml of wild-type hIL13 consistently produced a maximal proliferative response in TF-1 cells of ~300% that of the baseline value (FIG. 3, panel A). Differences were observed in TF-1 cell proliferation depending on whether the mutants were in the predicted alpha-helices A, C, or D. Of the alpha-helix A mutants, hIL13.E13K induced only a minimal proliferative response over the range tested (FIG. 3, panel B), and hIL13.E13I, hIL13.E13S, and hIL13.E13Y failed to induce any proliferative response (FIG. 3, panel B). Mutants hIL13.E13D and, unexpectedly, hIL13.E13R both induced a dose-dependent increase in proliferation of the TF-1 cells. Their induction of TF-1 cell proliferation followed the same pattern as wild-type hIL13, although hIL13.E13D had a lesser effect on proliferation than did hIL13.E13R (FIG. 3, panel A). Both hIL13.E16K and hIL13.E17K (with mutated sites one turn of the alpha-helix up from position 13) induced a dose-dependent increase in the proliferative response of the TF-1 cells (FIG. 3, panel A). While the hIL13.E17K-induced effect was comparable to wild-type hIL13, the hIL13.E16K-induced effect was significantly greater than that caused by wild-type hIL13.

The alpha-helix C mutants, hIL13.R66D and hIL13.S69D, both showed a significantly impaired ability to stimulate TF-1 cells, compared to wild-type hIL13 (FIG. 3, panel C) Their action on TF-1 cells, however, can be classified between that caused by mutants shown in FIG. 3, panels A and B. The alpha-helix D mutants also exhibited contrasting patterns of action on TF-1 cells. The hIL13.F113D mutant was equivalent to wild-type hIL13 in inducing TF-1 cell proliferation, while the hIL13.R109D mutant was inactive on these cells (not shown).

The ability of the hIL13 mutants to interact with the shared hIL13/4 receptor on normal cells was assessed by examining their effect on VCAM-1 expression on the surface of HUVEC. Cytokine binding of the shared IL13/4 receptor on the HUVEC cell surface results in transmembrane signaling events that induce VCAM-1 expression on these cells. Results from two separate experiments are shown in FIG. 4. Cells incubated in the absence of hIL13 showed minimal, nonspecific VCAM-1 staining (FIG. 4, panels A and G). In contrast, cells incubated overnight in media containing wild-type hIL13 exhibited a marked increase in VCAM-1 (FIG. 4, panels B and H). The pattern of the staining appeared to be specific for certain areas of the cell surface, compared to the minimal, homogeneous staining of cells that had not been incubated with cytokine (FIG. 4, panels A and G). Cells incubated with mutants hIL13.E13I, hIL13.E13K, and hIL13.E13Y, which are unable to induce TF-1 cell proliferation (FIG. 3), showed less VCAM-1 expression than those treated with wild-type hIL13 (FIG. 4, panels C, D, F, and B, respectively). Although mutant hIL13.F113D was not tested, the hIL13.R109D-induced VCAM-1 staining was negligible (not shown), suggesting again the involvement of alpha-helix D of the cytokine in effective signaling through the shared receptor. Cells treated with mutants hIL13.E13R and hIL13.E17K showed an increase in VCAM-1 staining similar to that induced by wild-type hIL13, when compared to their respective controls (FIG. 4, panels E and J). Mutant hIL13.E16K appeared to have a superagonistic effect on VCAM-1 expression compared to its wild-type IL13 control (FIG. 4, panels I and H, respectively).

The ability of hIL13 and its mutants to block the cancer-restrictive hIL13 receptor on two different human glioblastoma cell lines was examined in cytotoxicity assays using hIL13-PE1E, an extremely potent anti-tumor agent on glioma cells (see Debinski et al. (1996) J. Biol. Chem., 271: 22428–22433). The cytotoxin caused a high level of cytotoxicty in cultured U-251-MG cells (FIG. 5, panel A) and SNB-19 cells (FIG. 5, panel B) when the cells were cultured in the absence of a competing ligand for the receptor. When cultured in the presence of hIL13 or any of its A or C helix mutants, the level of cytotoxicity was reduced even at the highest concentration of cytotoxin used (FIG. 5, panels A and B). $IC_{50}$s for tests without blocking ligand were 0.1 ng/ml (1.25 pM) for U-251-MG cells and 0.07 ng/ml (0.875 pM) for SNB-19 cells. In contrast, the blocking assay using hIL13 mutants showed their ability to increase the $IC_{50}$ by at least 100 times. For concentrations of hIL13 or its mutants up to 1000× (by weight) over hIL13-PE1E, no discernable differences were detected between these various mutants and wild-type hIL13 in blocking the cytotoxin's activity on the glioma cells (FIG. 5, panels A and B). hIL13.F113D, an alpha-helix D mutant, behaved as the wild-type cytokine. In contrast, addition of hIL13.R109D to the cell cultures did not reduce the cytotoxin-induced cytotoxicity. hIL4 did not display any neutralizing activity in these assays.

Other Embodiments

This description has been by way of example of how the compositions and methods of invention can be made and carried out. Those of ordinary skill in the art will recognize that various details may be modified in arriving at the other detailed embodiments, and that many of these embodiments will come within the scope of the invention.

Therefore, to apprise the public of the scope of the invention and the embodiments covered by the invention, the following claims are made.

What is claimed is:

1. A composition comprising a mutant hIL13 molecule comprising a polypeptide having an amino acid sequence selected from the group consisting of SEQ ID NOs: 2, 3, and 5–12.

2. The composition of claim 1, wherein the molecule is a polypeptide consisting of an amino acid sequence selected from the group consisting of SEQ ID NOs: 2, 3, and 5–12.

3. The composition of claim 1, wherein the amino acid sequence has the sequence of SEQ ID NO:2.

4. The composition of claim 1, wherein the amino acid sequence has the sequence of SEQ ID NO:3.

5. The composition of claim 1, wherein the amino acid sequence has the sequence of SEQ ID NO:5.

6. The composition of claim 1, wherein the amino acid sequence has the sequence of SEQ ID NO:6.

7. The composition of claim 1, wherein the amino acid sequence has the sequence of SEQ ID NO:7.

8. The composition of claim 1, wherein the amino acid sequence has the sequence of SEQ ID NO:8.

9. The composition of claim 1, wherein the amino acid sequence has the sequence of SEQ ID NO:9.

10. The composition of claim 1, wherein the amino acid sequence has the sequence of SEQ ID NO:10.

11. The composition of claim 1, wherein the amino acid sequence has the sequence of SEQ ID NO:11.

12. The composition of claim 1, wherein the amino acid sequence has the sequence os SEQ ID NO:12.

13. The composition of claim 1, further comprising a pharmaceutically acceptable carrier.

14. The composition of claim 1, wherein the mutant molecule is conjugated to an effector molecule.

15. The composition of claim 14, wherein the effector molecule is selected from the group consisting of a cytotoxin, a detectable label, an antibody, a liposome, and a lipid.

16. The composition of claim 15, wherein the effector molecule is a cytotoxin selected from the group consisting of a Pseudomonas exotoxin, Diptheria toxin, ricin, abrin, saporin, and pokeweed viral protein.

17. The chimeric molecule of claim 16, wherein the cytotoxin is selected from the group consisting of PE38QQR, PE1E, and PE4E.

18. The chimeric molecule of claim 15, wherein the effector molecule comprises a radionuclide.

19. A method of delivering a mutant hIL13 molecule to a cell comprising the steps of:

providing a mutant hIL13 molecule comprising a polypeptide having an amino acid sequence selected from the group consisting of SEQ ID NOs:2, 3, and 5–12;

providing a cell; and contacting the cell with the mutant hIL13 molecule.

20. The method of claim 19, wherein the mutant hIL13 is conjugated to an effector molecule.

21. The method of claim 20, wherein the effector molecule is selected from the group consisting of a cytotoxin, a detectable label, an antibody, a liposome, and a lipid.

22. The method of claim 21, wherein the effector molecule is a cytotoxin selected from the group consisting of a Pseudomonas exotoxin, Diptheria toxin, ricin, abrin, saporin, and pokeweed viral protein.

23. The method of claim 22, wherein the cytotoxin is selected from the group consisting of PE38QQR, PE1E, and PE4E.

24. The method of claim 20, wherein the effector molecule comprises a radionuclide.

* * * * *

UNITED STATES PATENT AND TRADEMARK OFFICE
CERTIFICATE OF CORRECTION

PATENT NO. : 6,576,232 B1
APPLICATION NO. : 09/679710
DATED : June 10, 2003
INVENTOR(S) : Debinski It is certified that error appears in the above-identified patent and that said Letters Patent is hereby corrected as shown below:

In the section, STATEMENT AS TO FEDERALLY FUNDED RESEARCH, replace "This invention was made in part with Government support under grant CA741145 awarded by the National Institutes of Health. The Government may have certain rights in the invention." with --This invention was made with Government support under Grant No. CA74145, awarded by the National Institutes of Health. The Government has certain rights in the invention.--

Signed and Sealed this

Twelfth Day of August, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,576,232 B1 | Page 1 of 1 |
| APPLICATION NO. | : 09/679710 | |
| DATED | : June 10, 2003 | |
| INVENTOR(S) | : Waldemar Debinski et al. | |

It is certified that error appears in the above-identified patent and that said Letters Patent is hereby corrected as shown below:

Col. 45 line 20
In the Sequence Listing, SEQ ID NO. 23, field <223>, replace "113" with --114--.

Signed and Sealed this

Fourth Day of August, 2009

JOHN DOLL
*Acting Director of the United States Patent and Trademark Office*